(12) United States Patent
Cameron et al.

(10) Patent No.: US 10,412,997 B2
(45) Date of Patent: *Sep. 17, 2019

(54) ELECTRONIC VAPORIZING DEVICE WITH MESSAGING FUNCTIONALITY

(71) Applicant: Lunatech, LLC, Studio City, CA (US)

(72) Inventors: John David Cameron, Studio City, CA (US); Dean Becker, Fairhope, AL (US); Gene Fein, Oxnard, CA (US)

(73) Assignee: LunaTech, LLC, Encino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/204,072

(22) Filed: Nov. 29, 2018

(65) Prior Publication Data

US 2019/0090547 A1 Mar. 28, 2019

Related U.S. Application Data

(63) Continuation of application No. 15/600,643, filed on May 19, 2017, now abandoned, and a continuation-in-part of application No. 15/493,804, filed on Apr. 21, 2017, which is a continuation of application No. 15/495,609, filed on Apr. 24, 2017, now abandoned.

(60) Provisional application No. 62/339,481, filed on May 20, 2016.

(51) Int. Cl.
*A24F 13/00* (2006.01)
*A24F 47/00* (2006.01)
*H04W 4/12* (2009.01)
*A61K 9/00* (2006.01)
*A24B 15/16* (2006.01)

(52) U.S. Cl.
CPC .......... *A24F 47/008* (2013.01); *A24B 15/167* (2016.11); *A61K 9/0073* (2013.01); *H04W 4/12* (2013.01)

(58) Field of Classification Search
CPC ...................................... A24F 47/00
USPC ................................. 131/328–329
See application file for complete search history.

(56) References Cited

U.S. PATENT DOCUMENTS

2017/0332702 A1* 11/2017 Cameron ............. A61K 9/0073

* cited by examiner

*Primary Examiner* — Phuong K Dinh
(74) *Attorney, Agent, or Firm* — Susan L. McCain; Hankin Patent Law, APC

(57) ABSTRACT

The present disclosure is directed to an electronic vaporizing device having messaging functionality. The electronic vaporizing device may be configured to send and receive messages to other electronic vaporizing devices, electronic communication devices, and the like. In one embodiment, the messages may include information associated with the type and amount of material to be vaporized. The electronic vaporizing device may include a mixing component operable to withdraw a selected amount of vaporizable material from one or more of the containers to produce a vaporizable mixture according to the information included in the messages.

18 Claims, 17 Drawing Sheets

ELECTRONIC VAPORIZING DEVICE WITH MESSAGING FUNCTIONALITY

CROSS-REFERENCE TO RELATED APPLICATION

This application claims the benefit of U.S. Non-Provisional patent application Ser. No. 15/600,643, filed on May 19, 2017, which claims the benefit of and priority to U.S. Provisional Application No. 62/339,481, filed on May 20, 2016, entitled "Electronic Vapor Device for Messaging", U.S. patent application Ser. No. 15/493,804, filed on Apr. 21, 2017, entitled "Natural-Based Liquid Composition and Electronic Vaporizing Devices for Using Such Compositions", and U.S. patent application Ser. No. 15/495,609, filed on Apr. 24, 2017, entitled "Electronic Vaporizing Device for Vaporizing Water-Based Compositions", the contents of which are incorporated herein by reference as though set forth in their entireties.

BACKGROUND

Various types of personal vaporizers have been known in the art for many years. In general, currently available vaporizers are characterized by heating a solid to a smoldering point, vaporizing a liquid by direct or indirect heat, or nebulizing a liquid by heat and/or by expansion through a nozzle. Such devices are designed to release aromatic materials held in a solid or liquid form, while avoiding high temperatures that may result in combustion and associated formation of tars, carbon monoxide, or other harmful combustion byproducts. Preferably, the device releases a vapor or very fine mist with a mouth feel similar to smoke, under suction. Thus, a vaporizing device may be made to mimic traditional smoking articles, such as cigarettes, cigars, pipes, and hookahs in certain aspects, while avoiding significant adverse health effects of traditional tobacco or other herbal consumption. While various designs are long known, it is only relatively recently that technology has improved and markets have developed to the point to make mass-marketing of personal vaporizers practical. It would be desirable, therefore, to develop new technologies for introducing a messaging function to the act of vaporizing.

SUMMARY

The following presents a simplified overview of the example embodiments in order to provide a basic understanding of some embodiments of the example embodiments. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented hereinbelow. It is to be understood that both the following general description and the following detailed description are exemplary and explanatory only and are not restrictive.

In accordance with the embodiments disclosed herein, the present disclosure is directed to an electronic vaporizing device with messaging functionality. In one embodiment, there may be provided a system, method, and electronic vaporizing device configured to send and receive messages to other electronic vaporizing devices, electronic communication devices, and the like. In one embodiment, the messages may include information associated with the type and amount of material to be vaporized. The electronic vaporizing device may include a mixing component operable to withdraw a selected amount of vaporizable material from one or more of the containers to produce a vaporizable mixture according to the information included in the messages.

In accordance with the embodiments disclosed herein, there may be provided an electronic vaporizing device. The electronic vaporizing device may comprise a device processor operable for controlling the electronic vaporizing device, at least one container for storing a vaporizable material, and a mixing component operatively coupled to the device processor and controlled in part by the device processor, wherein the mixing component may be in fluid communication with the at least one container for receiving at least a portion of the vaporizable material therefrom, wherein the mixing component may be operable to withdraw a selected amount of vaporizable material from at least one container. The electronic vaporizing device may further comprise a vaporizing component operatively coupled to the device processor and controlled in part by the device processor, wherein the vaporizing component may be in fluid communication with the mixing component for receiving at least a portion of the vaporizable material withdrawn from the at least one container by the mixing component, wherein the vaporizing component may be operable to vaporize the vaporizable material received therein, and at least one vapor outlet coupled to the vaporizing component and configured to receive vapor generated by the vaporizing component, the at least one vapor outlet operable to expel the generated vapor from the vaporizing device. The electronic vaporizing device may also comprise an input/output device operatively coupled to the device processor and configured to operatively connect the device processor to an associated electronic communication device, wherein the input/output device may be configured to receive a plurality of electronic communications from the associated electronic communication device, wherein the plurality of received communications may comprise at least one of an instant message, a Short Message Service message, a Multimedia Messaging Service message, and an Enhanced Messaging Service message, and wherein at least one of the received communications may include at least one command for controlling at least one operational parameter of the electronic vaporizing device. The input/output device may also be configured to transmit the at least one command to the device processor for controlling at least one operational parameter of the electronic vaporizing device. The electronic vaporizing device may further comprise at least one power source operatively coupled to the mixing component and the vaporizing component, wherein the at least one power source may be operable to generate a supply of power for operation of at least the mixing component, the vaporizing component, and combinations thereof.

In one embodiment, the device processor may be operable to generate at least one control signal for controlling at least one operational parameter of the electronic vaporizing device based on the at least one received command. In one embodiment, the device processor may be operable to generate at least one mixing control signal for controlling at least one operational parameter of the mixing component based on the at least one received command. The at least one command may include at least one of: an identification of the at least one container from which the selected amount of vaporizable material is withdrawn, the selected amount of vaporizable material withdrawn from the at least one container, and combinations thereof.

In another embodiment, the at least one container may be a plurality of containers, wherein each container may be configured to store a vaporizable material. In one embodiment, the device processor may be operable to generate at least one mixing control signal for controlling an amount of vaporizable material to be withdrawn from a selected number of the plurality of containers by the mixing component based on the at least one command. The at least one command may include an identification of each of: a selected number of the plurality of containers from which the selected amount of vaporizable material is withdrawn and the selected amount of vaporizable material withdrawn from the selected number the plurality of containers. In one embodiment, at least two of the selected number of the plurality of containers may be configured to each store a discrete vaporizable material.

In accordance with the embodiments disclosed herein, there may be provided a system for operation an electronic vaporizing device in conjunction with an electronic communication device. The electronic vaporizing device may comprise a first processor operable for controlling the electronic vaporizing device, at least one container for storing a vaporizable material, and a mixing component operatively coupled to the first processor and controlled in part by the first processor, wherein the mixing component may be in fluid communication with the at least one container for receiving at least a portion of the vaporizable material therefrom, wherein the mixing component may be operable to withdraw a selected amount of vaporizable material from at least one container. The electronic vaporizing device may further comprise a vaporizing component operatively coupled to the first processor and controlled in part by the first processor, wherein the vaporizing component may be in fluid communication with the mixing component for receiving at least a portion of the vaporizable material withdrawn from the at least one container by the mixing component, wherein the vaporizing component may be operable to vaporize the vaporizable material received therein, and at least one vapor outlet coupled to the vaporizing component and configured to receive vapor generated by the vaporizing component, the at least one vapor outlet operable to expel the generated vapor from the vaporizing device. The electronic vaporizing device may also comprise an input/output device operatively coupled to the first processor and configured to operatively connect the first processor to the electronic communication device, wherein the input/output device may be configured to receive a plurality of electronic communications from the electronic communication device, wherein at least one of the received communications may include at least one command for controlling at least one operational parameter of the electronic vaporizing device. The input/output device may also be configured to transmit the at least one command to the first processor for controlling at least one operational parameter of the electronic vaporizing device. The electronic vaporizing device may further comprise at least one power source operatively coupled to the mixing component and the vaporizing component, wherein the at least one power source may be operable to generate a supply of power for operation of at least the mixing component, the vaporizing component, and combinations thereof.

The electronic communication device may comprise a second processor operable for controlling the electronic communication device and a network access component operatively coupled to the second processor and configured to connect to at least one network, wherein the network access component may be operable to receive a plurality of electronic communications from the at least one network, wherein the plurality of received communications may comprise at least one of an instant message, a Short Message Service message, a Multimedia Messaging Service message, and an Enhanced Messaging Service message, wherein at least one of the received communications may include at least one command for controlling at least one operational parameter of the electronic vaporizing device. The electronic communication device may further comprise an input/output port operatively coupled to the first processor of the electronic vaporizing device and configured to transmit the plurality of communications received from the at least one network to the electronic vaporizing device, wherein at least one of the received communications may include at least one command for controlling at least one operational parameter of the electronic vaporizing device. The electronic communication device may also comprise at least one electronic communication device power source operatively connected to the second processor and operable to generate a supply of power for operation of at least the electronic communication device.

In one embodiment, the first processor may be operable to generate at least one control signal for controlling at least one operational parameter of the electronic vaporizing device based on the at least one received command. In one embodiment, the first processor may be operable to generate at least one mixing control signal for controlling at least one operational parameter of the mixing component based on the at least one received command. The at least one command may include at least one of: an identification of the at least one container from which the selected amount of vaporizable material is withdrawn, the selected amount of vaporizable material withdrawn from the at least one container, and combinations thereof.

In another embodiment, the at least one container may be a plurality of containers, wherein each container may be configured to store a vaporizable material. In one embodiment, the first processor may be operable to generate at least one mixing control signal for controlling an amount of vaporizable material to be withdrawn from a selected number of the plurality of containers by the mixing component based on the at least one command. The at least one command may include an identification of each of: a selected number of the plurality of containers from which the selected amount of vaporizable material is withdrawn and the selected amount of vaporizable material withdrawn from the selected number the plurality of containers.

In one embodiment, the second processor may be operable to generate a plurality of electronic communications, wherein the plurality of generated communications may comprise at least one of an instant message, a Short Message Service message, a Multimedia Messaging Service message, and an Enhanced Messaging Service message, and wherein the network access component may be operable to transmit the plurality of generated communications to the at least one network.

In accordance with the embodiments disclosed herein, a method may be provided for vaporizing at least one vaporizable material by an electronic vaporizing device, wherein the electronic vaporizing device may comprise (a) a plurality of containers, each containing a vaporizable material; (b) a mixing component operable to control a selected amount of vaporizable material to be withdrawn from at least one container of the plurality of containers; (c) a vaporizing component operable to vaporize a plurality of materials received therein and expel a generated vapor from the vaporizing component; and (d) at least one power source operatively coupled to the mixing component and the vaporizing component The method may comprise receiving, from an associated electronic communication device, a plurality of electronic communications, wherein the plurality of received communications may comprise at least one of an instant message, a Short Message Service message, a Multimedia Messaging Service message, and an Enhanced Messaging Service message, and wherein at least one of the received communications may include at least one command for controlling at least one operational parameter of the electronic vaporizing device. The method may further comprise generating at least one control signal for controlling at least one operational parameter of the electronic vaporizing device based on the at least one received command. The method may also comprise withdrawing, by the mixing component, a selected amount of vaporizable material from the at least one container in accordance with the at least one control signal and delivering the selected amount of vaporizable material withdrawn therefrom to the vaporizing component, and vaporizing at least a portion of the received vaporizable material by the vaporizing component in accordance with the at least one control signal to generate a vapor therefrom.

In one embodiment, the step of generating at least one control signal may comprise generating at least one mixing control signal for controlling an amount of vaporizable material to be withdrawn from a selected number of the plurality of containers by the mixing component based on the at least one command. The at least one command may include an identification of each of: a selected number of the plurality of containers from which the selected amount of vaporizable material is withdrawn and the selected amount of vaporizable material withdrawn from the selected number the plurality of containers.

In another embodiment, the method may further comprise receiving a plurality of electronic communications from the at least one network, wherein the plurality of received communications may comprise at least one of an instant message, a Short Message Service message, a Multimedia Messaging Service message, and an Enhanced Messaging Service message receiving, by the electronic communication device, and wherein at least one of the received communications may include at least one command for controlling at least one operational parameter of the electronic vaporizing device.

Still other advantages, embodiments, and features of the subject disclosure will become readily apparent to those of ordinary skill in the art from the following description wherein there is shown and described a preferred embodiment of the present disclosure, simply by way of illustration of one of the best modes best suited to carry out the subject disclosure As it will be realized, the present disclosure is capable of other different embodiments and its several details are capable of modifications in various obvious embodiments all without departing from, or limiting, the scope herein. Accordingly, the drawings and descriptions will be regarded as illustrative in nature and not as restrictive.

BRIEF DESCRIPTION OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps which are illustrated. When the same numeral appears in different drawings, it refers to the same or like components or steps.

DETAILED DESCRIPTION OF THE ILLUSTRATIVE EMBODIMENTS

Figure 1A:
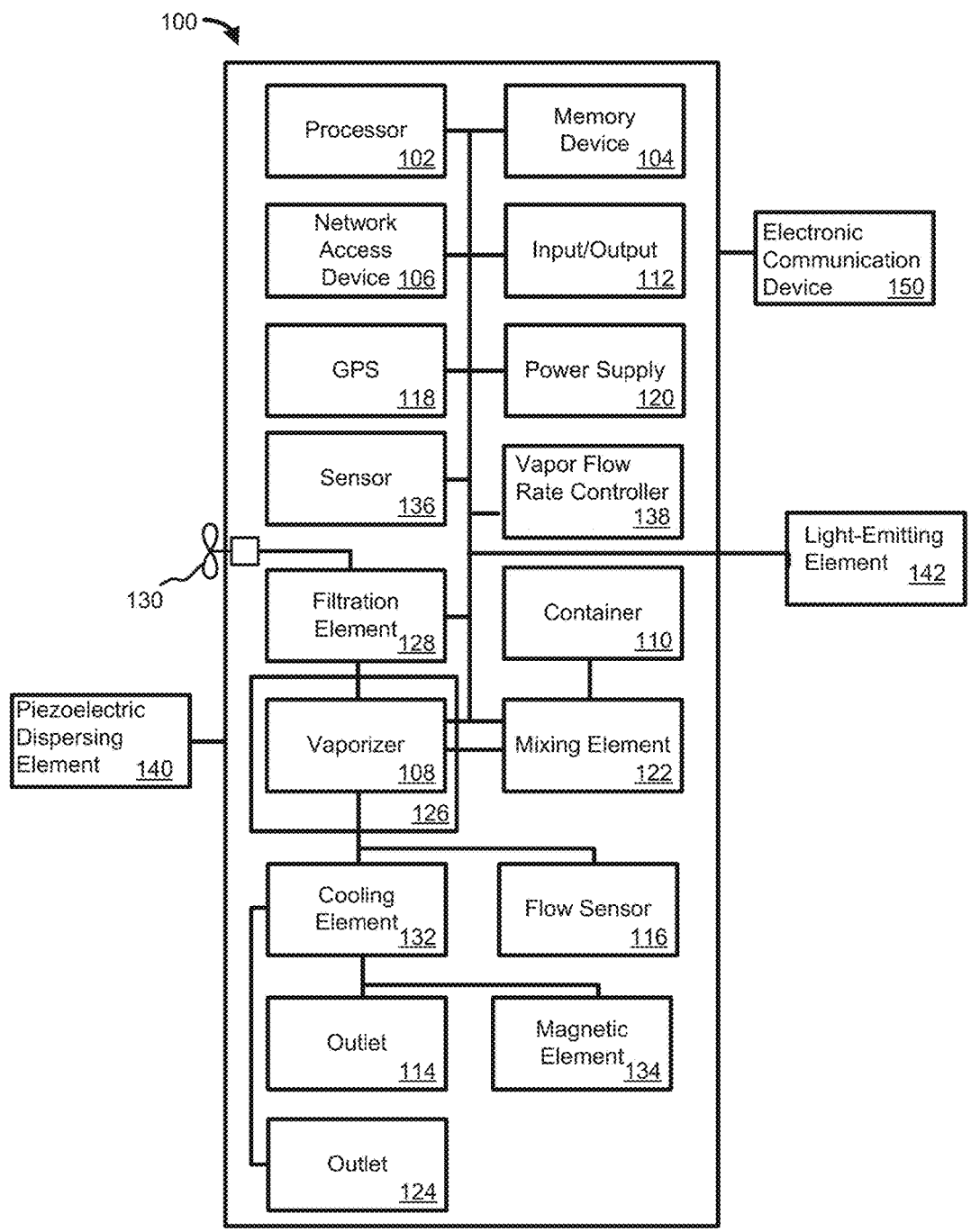
FIGS. 1A and 1B illustrate block diagrams of one embodiment of an electronic vaporizing device according to some embodiments.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value.

Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all embodiments of this application including, but not limited to, steps in disclosed methods. Thus, if there are a variety of additional steps that may be performed it is understood that each of these additional steps may be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware embodiments. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, may be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that may direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, may be implemented by special purpose hardware-based computer systems that perform the specified functions or steps, or combinations of special purpose hardware and computer instructions.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", may refer to a deviance of between 0.001-10% from the indicated number or range of numbers.

Various embodiments are now described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form to facilitate describing these embodiments.

In various implementations, the electronic vaporizing device may be configured to send and receive messages to other electronic vaporizing devices, electronic communication devices, and the like. In one embodiment, the messages may include information associated with the type and amount of material to be vaporized. The electronic vaporizing device may include a mixing component operable to withdraw a selected amount of vaporizable material from one or more of the containers to produce a vaporizable mixture according to the information included in the messages.

Figure 1B:
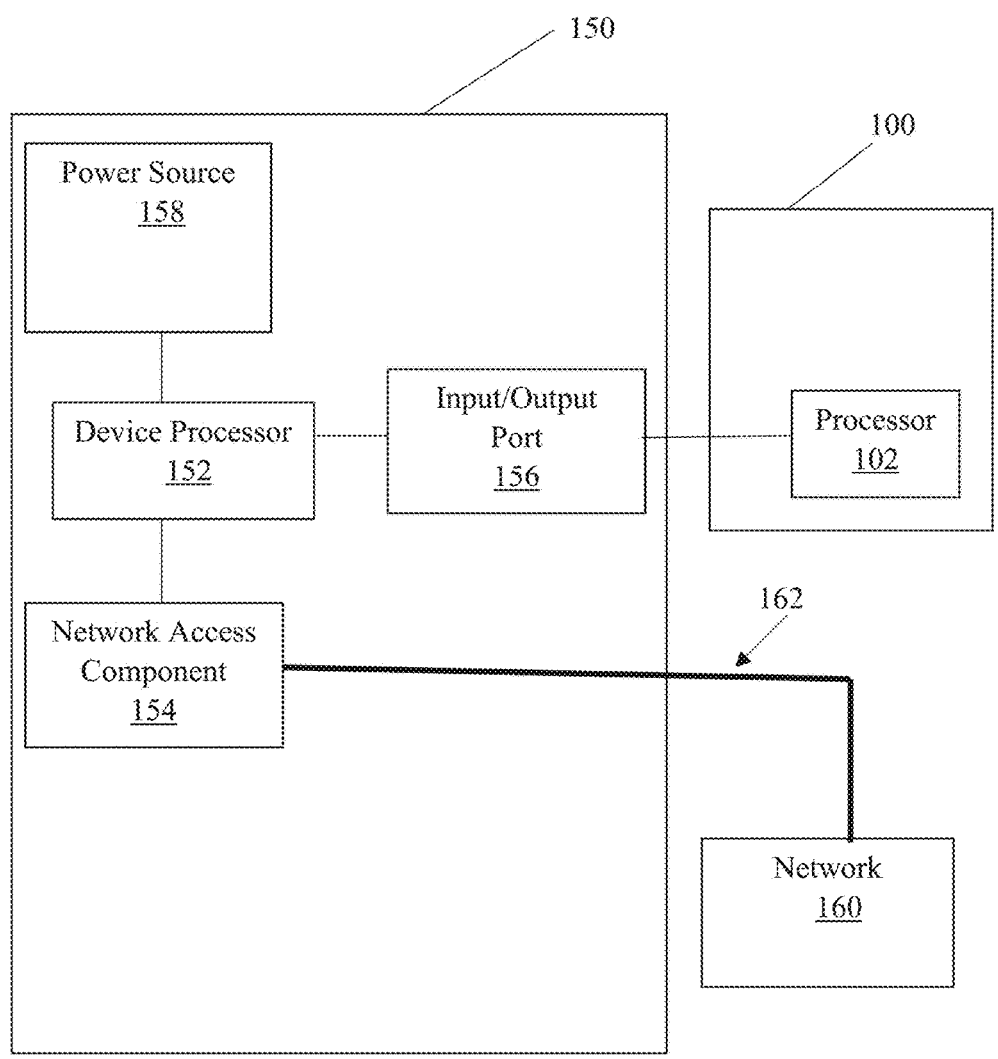

FIGS. 1A and 1B are block diagrams of one embodiment of an electronic vaporizing device 100 as described herein. The electronic vaporizing device 100 may be, for example, an electronic cigarette, an electronic cigar, an electronic vapor device, a hybrid electronic communication device coupled/integrated vapor device, a robotic vapor device, a modified vapor device ("mod"), a micro-sized electronic vapor device, and the like. The electronic vaporizing device 100 may comprise any suitable housing for enclosing and protecting the various components disclosed herein. The electronic vaporizing device 100 may comprise a processor 102 operable to control the operation of the electronic vaporizing device 100. The processor 102 may be, or may comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU), for example, one based on 80×86 architecture as designed by Intel™ or AMD™, or a system-on-a-chip as designed by ARM™. The processor 102 may be coupled (e.g., communicatively, operatively, etc.) to auxiliary devices or modules of the electronic vaporizing device 100 using a bus or other coupling. The electronic vaporizing device 100 may comprise power supply 120. The power supply 120 may comprise one or more batteries and/or other power storage device (e.g., capacitor) and/or a port for connecting to an external power supply. The one or more batteries may be rechargeable. The one or more batteries may comprise a lithium-ion battery (including thin film lithium ion batteries), a lithium-ion polymer battery, a nickel-cadmium battery, a nickel metal hydride battery, a lead-acid battery, combinations thereof, and the like. For example, an external power supply may supply power to the electronic vaporizing device 100 and a battery may store at least a portion of the supplied power.

The electronic vaporizing device 100 may comprise a memory device 104 coupled to the processor 102. The memory device 104 may comprise a random access memory (RAM) configured for storing program instructions and data for execution or processing by the processor 102 during control of the electronic vaporizing device 100. When the electronic vaporizing device 100 is powered off or in an inactive state, program instructions and data may be stored in a long-term memory, for example, a non-volatile magnetic optical, or electronic memory storage device (not shown). At least one of the RAM or the long-term memory may comprise a non-transitory computer-readable medium storing program instructions that, when executed by the processor 102, cause the electronic vaporizing device 100 to perform all or part of one or more methods and/or operations described herein. Program instructions may be written in any suitable high-level language, for example, C, C++, C# or the Java™, and compiled to produce machine-language code for execution by the processor 102.

In one embodiment, the electronic vaporizing device 100 may comprise a network access device 106 allowing the electronic vaporizing device 100 to be coupled to one or more ancillary devices (not shown) such as via an access point (not shown) of a wireless telephone network, local area network, or other coupling to a wide area network, for example, the Internet. In that regard, the processor 102 may be configured to share data with the one or more ancillary devices via the network access device 106. The shared data may comprise, for example, usage data and/or operational data of the electronic vaporizing device 100, a status of the electronic vaporizing device 100, a status and/or operating condition of one or more the components of the electronic vaporizing device 100, text to be used in a message, a product order, payment information, and/or any other data. Similarly, the processor 102 may be configured to receive control instructions from the one or more ancillary devices via the network access device 106. For example, a configuration of the electronic vaporizing device 100, an operation of the electronic vaporizing device 100, and/or other settings of the electronic vaporizing device 100, may be controlled by the one or more ancillary devices via the network access device 106. For example, an ancillary device may comprise a server that may provide various services and another ancillary device may comprise a smartphone for controlling operation of the electronic vaporizing device 100. In some embodiments, the smartphone or another ancillary device may be used as a primary input/output of the electronic vaporizing device 100 such that data may be received by the electronic vaporizing device 100 from the server, transmitted to the smartphone, and output on a display of the smartphone. In an embodiment, data transmitted to the ancillary device may comprise a mixture of vaporizable material and/or instructions to release vapor. For example, the electronic vaporizing device 100 may be configured to determine a need for the release of vapor into the atmosphere. The electronic vaporizing device 100 may provide instructions via the network access device 106 to an ancillary device (e.g., another vapor device) to release vapor into the atmosphere.

In an embodiment, the electronic vaporizing device 100 may also comprise an input/output device 112 coupled to one or more of the processor 102, the vaporizer 108, the network access device 106, and/or any other electronic component of the electronic vaporizing device 100. Input may be received from a user or another device and/or output may be provided to a user or another device via the input/output device 112. The input/output device 112 may comprise any combinations of input and/or output devices such as buttons, knobs, keyboards, touchscreens, displays, light-emitting elements, a speaker, and/or the like. In an embodiment, the input/output device 112 may comprise an interface port (not shown) such as a wired interface, for example a serial port, a Universal Serial Bus (USB) port, an Ethernet port, or other suitable wired connection. The input/output device 112 may comprise a wireless interface (not shown), for example a transceiver using any suitable wireless protocol, for example Wi-Fi (IEEE 802.11), Bluetooth®, infrared, or other wireless standard. For example, the input/output device 112 may communicate with a smartphone via Bluetooth® such that the inputs and outputs of the smartphone may be used by the user to interface with the electronic vaporizing device 100. In an embodiment, the input/output device 112 may comprise a user interface. The user interface may comprise at least one of lighted signal lights, gauges, boxes, forms, check marks, avatars, visual images, graphic designs, lists, active calibrations or calculations, 2D interactive fractal designs, 3D fractal designs, 2D and/or 3D representations of vapor devices and other interface system functions.

In an embodiment, the input/output device 112 may comprise a touchscreen interface and/or a biometric interface. For example, the input/output device 112 may include controls that allow the user to interact with and input information and commands to the electronic vaporizing device 100. For example, with respect to the embodiments described herein, the input/output device 112 may comprise a touch screen display. The input/output device 112 may be configured to provide the content of the exemplary screen shots shown herein, which are presented to the user via the functionality of a display. User inputs to the touch screen display are processed by, for example, the input/output device 112 and/or the processor 102. The input/output device 112 may also be configured to process new content and communications to the electronic vaporizing device 100. The touch screen display may provide controls and menu selections, and process commands and requests. Application and content objects may be provided by the touch screen display. The input/output device 112 and/or the processor 102 may receive and interpret commands and other inputs, interface with the other components of the electronic vaporizing device 100 as required. In an embodiment, the touch screen display may enable a user to lock, unlock, or partially unlock or lock, the electronic vaporizing device 100. The electronic vaporizing device 100 may be transitioned from an idle and locked state into an open state by, for example, moving or dragging an icon on the screen of the electronic vaporizing device 100, entering in a password/passcode, and the like. The input/output device 112 may thus display information to a user such as a puff count, an amount of vaporizable material remaining in the container 110, battery remaining, signal strength, combinations thereof, and the like.

In an embodiment, the input/output device 112 may comprise an audio user interface. A microphone may be configured to receive audio signals and relay the audio signals to the input/output device 112. The audio user interface may be any interface that is responsive to voice or other audio commands. The audio user interface may be configured to cause an action, activate a function, etc., by the electronic vaporizing device 100 (or another device) based on a received voice (or other audio) command. The audio user interface may be deployed directly on the electronic vaporizing device 100 and/or via other electronic devices (e.g., electronic communication devices, such as a smartphone, a smart watch, a tablet, a laptop, a dedicated audio user interface device, other personal computing devices, and the like). The audio user interface may be used to control the functionality of the electronic vaporizing device 100. Such functionality may comprise, but is not limited to, custom mixing of vaporizable material (e.g., eLiquids) and/or ordering custom made eLiquid combinations via an eCommerce service (e.g., specifications of a user's custom flavor mix may be transmitted to an eCommerce service, so that an eLiquid provider may mix a custom eLiquid cartridge for the user). The user may then reorder the custom flavor mix anytime or even send it to friends as a present, all via the audio user interface. The user may also send via voice command a mixing recipe to other users. The other users may utilize the mixing recipe (e.g., via an electronic vapor device having multiple chambers for eLiquid) to sample the same mix via an auto-order to the other users' devices to create the received mixing recipe. A custom mix may be given a title by a user and/or may be defined by parts (e.g., one part liquid A and two parts liquid B). The audio user interface may also be utilized to create and send a custom message to other users, to join electronic vaporizing clubs, to receive electronic vaporizing chart information, and to conduct a wide range of social networking, location services and eCommerce activities. The audio user interface may be secured via a password (e.g., audio password) which features at least one of tone recognition, other voice quality recognition and, in one embodiment, may utilize at least one special cadence as part of the audio password.

The input/output device 112 may be configured to interface with other devices, for example, exercise equipment, computing equipment, communications devices and/or other vapor devices, for example, via a physical or wireless connection. The input/output device 112 may thus exchange data with the other equipment. A user may sync their electronic vaporizing device 100 to other devices, via programming attributes such as mutual dynamic link library (DLL) 'hooks'. This enables a smooth exchange of data between devices, as may a web interface between devices. The input/output device 112 may be used to upload one or more profiles to the other devices. Using exercise equipment as an example, the one or more profiles may comprise data such as workout routine data (e.g., timing, distance, settings, heart rate, etc.) and vaping data (e.g., eLiquid mixture recipes, supplements, vaping timing, etc.). Data from usage of previous exercise sessions may be archived and shared with new electronic vapor devices and/or new exercise equipment so that history and preferences may remain continuous and provide for simplified device settings, default settings, and recommended settings based upon the synthesis of current and archival data.

In an embodiment, the input/output device 112 may be configured to interface with an electronic communication device 150. The input/output device 112 may operatively connect the processor 102 with the electronic communication device 150.

As shown in FIG. 1B, the electronic communication device 150 may be operable to interface with at least one network 160 via communication link 162 to receive a plurality of electronic communications from the at least one network 160. The plurality of received communications may include at least one of an instant message, a Short Message Service message, a Multimedia Messaging Service message, and an Enhanced Messaging Service message. At least one of the received communications may include at least one command for controlling at least one operational parameter of the electronic vaporizing device 100. The electronic communication device 150 may transmit the plurality of received communications to the electronic vaporizing device 100, wherein at least one of the received communications may include at least one command for controlling at least one operational parameter of the electronic vaporizing device 100.

As shown in FIG. 1A, in an embodiment, the electronic vaporizing device 100 may comprise a vaporizer 108. The vaporizer 108 may be coupled to one or more containers 110. Each of the one or more containers 110 may be configured to hold one or more vaporizable or non-vaporizable materials. The vaporizer 108 may receive the one or more vaporizable or non-vaporizable materials from the one or more containers 110 and heat the one or more vaporizable or non-vaporizable materials until the one or more vaporizable or non-vaporizable materials achieve a vapor state. In various embodiments, instead of heating the one or more vaporizable or non-vaporizable materials, the vaporizer 108 may nebulize or otherwise cause the one or more vaporizable or non-vaporizable materials in the one or more containers 110 to reduce in size into particulates. In various embodiments, the one or more containers 110 may comprise a compressed liquid that may be released to the vaporizer 108 via a valve or another mechanism. In various embodiments, the one or more containers 110 may comprise a wick (not shown) through which the one or more vaporizable or non-vaporizable materials is drawn to the vaporizer 108. The one or more containers 110 may be made of any suitable structural material, such as, an organic polymer, metal, ceramic, composite, or glass material. In one embodiment, the vaporizable material may comprise one or more, of a Propylene Glycol (PG) based liquid, a Vegetable Glycerin (VG) based liquid, a water based liquid, combinations thereof, and the like. In one embodiment, the vaporizable material may comprise Tetrahydrocannabinol (THC), Cannabidiol (CBD), combinations thereof, and the like. In a further embodiment, the vaporizable material may comprise an extract from duboisia hopwoodii.

In an embodiment, the electronic vaporizing device 100 may comprise a mixing element 122. The mixing element 122 may be coupled to the processor 102 to receive one or more control signals. The one or more control signals may instruct the mixing element 122 to withdraw specific amounts of fluid from the one or more containers 110. The mixing element may, in response to a control signal from the processor 102, withdraw select quantities of vaporizable material in order to create a customized mixture of different types of vaporizable material. The liquid withdrawn by the mixing element 122 may be provided to the vaporizer 108.

In an embodiment, input from the input/output device 112 may be used by the processor 102 to cause the vaporizer 108 to vaporize the one or more vaporizable or non-vaporizable materials. For example, a user may depress a button, causing the vaporizer 108 to start vaporizing or heating the one or more vaporizable or non-vaporizable materials. A user may then draw on an outlet 114 to inhale the vapor. In various embodiments, the processor 102 may control vapor production and flow to the outlet 114 based on data detected by a flow sensor 116. For example, as a user draws on the outlet 114, the flow sensor 116 may detect the resultant pressure and provide a signal to the processor 102. In response, the processor 102 may cause the vaporizer 108 to begin vaporizing the one or more vaporizable or non-vaporizable materials, terminate vaporizing the one or more vaporizable or non-vaporizable materials, and/or otherwise adjust a rate of vaporization of the one or more vaporizable or non-vaporizable materials. In another embodiment, the vapor may exit the electronic vaporizing device 100 through an outlet 124. The outlet 124 differs from the outlet 114 in that the outlet 124 may be configured to distribute the vapor into the local atmosphere, rather than being inhaled by a user. In an embodiment, vapor exiting the outlet 124 may be at least one of aromatic, medicinal, recreational, and/or wellness related.

In one embodiment, the electronic vaporizing device 100 may comprise a vapor flow rate control 138 interposed between the vaporizer 108 and at least one of outlet 114 and outlet 124. The vapor flow rate control 138 may be coupled to the processor 102 to receive one or more control signals for controlling a vapor flow rate through at least one of outlet 114 and outlet 124. In one embodiment, the vapor flow rate control 138 may be comprised of a plurality of valves for controlling a vapor flow rate through at least one of outlet 114 and outlet 124. In one embodiment, each of the valves may include a lumen of adjustable effective diameter for controlling a rate of vapor flow therethrough. The processor 102 may determine the vapor flow rate for at least one of outlet 114 and outlet 124 based on a type of vaporizable material stored in the at least one container, an amount of vaporizable material to be withdrawn from the at least one container, desired vapor output, timing of the withdrawal, user preferences, and the like, and combinations thereof. The vapor flow rate for outlet 114 and outlet 124 may be the same rate or different rates.

In another embodiment, the electronic vaporizing device 100 may comprise a piezoelectric dispersing element 140. In some embodiments, the piezoelectric dispersing element 140 may be charged by a battery, and may be driven by a processor on a circuit board. The circuit board may be produced using a polyimide such as Kapton®, or other suitable material. The piezoelectric dispersing element 140 may comprise a thin metal disc which causes dispersion of the fluid fed into the dispersing element via the wick or other soaked piece of organic material through vibration. Once in contact with the piezoelectric dispersing element 140, the vaporizable material (e.g., fluid) may be vaporized (e.g., turned into vapor or mist) and the vapor may be dispersed via a system pump and/or a sucking action of the user. In some embodiments, the piezoelectric dispersing element 140 may cause dispersion of the vaporizable material by producing ultrasonic vibrations. An electric field applied to a piezoelectric material within the piezoelectric dispersing element 140 may cause ultrasonic expansion and contraction of the piezoelectric material, resulting in ultrasonic vibrations to the disc. The ultrasonic vibrations may cause the vaporizable material to disperse, thus forming a vapor or mist from the vaporizable material.

In some embodiments, the connection between the power supply 120 and the piezoelectric dispersing element 140 may be facilitated using one or more conductive coils. The conductive coils may provide an ultrasonic power input to the piezoelectric dispersing element 140. For example, the signal carried by the coil may have a frequency of approximately 107.8 kHz. In some embodiments, the piezoelectric dispersing element 140 may comprise a piezoelectric dispersing element that may receive the ultrasonic signal transmitted from the power supply through the coils, and may cause vaporization of the vaporizable liquid by producing ultrasonic vibrations. An ultrasonic electric field applied to a piezoelectric material within the piezoelectric element causes ultrasonic expansion and contraction of the piezoelectric material, resulting in ultrasonic vibrations according to the frequency of the signal. The vaporizable liquid may be vibrated by the ultrasonic energy produced by the piezoelectric dispersing element 140, thus causing dispersal and/or atomization of the liquid. In an embodiment, the electronic vaporizing device 100 may be configured to permit a user to select between using a heating element of the vaporizer 108 or the piezoelectric dispersing element 140. In another embodiment, the electronic vaporizing device 100 may be configured to permit a user to utilize both a heating element of the vaporizer 108 and the piezoelectric dispersing element 140.

In an embodiment, the electronic vaporizing device 100 may comprise a heating casing 126. The heating casing 126 may enclose one or more of the container 110, the vaporizer 108, and/or the outlet 114. In a further embodiment, the heating casing 126 may enclose one or more components that make up the container 110, the vaporizer 108, and/or the outlet 114. The heating casing 126 may be made of ceramic, metal, and/or porcelain. The heating casing 126 may have varying thickness. In an embodiment, the heating casing 126 may be coupled to the power supply 120 to receive power to heat the heating casing 126. In another embodiment, the heating casing 126 may be coupled to the vaporizer 108 to heat the heating casing 126. In another embodiment, the heating casing 126 may serve as an insulator.

In an embodiment, the electronic vaporizing device 100 may comprise a filtration element 128. The filtration element 128 may be configured to remove (e.g., filter, purify, etc.) contaminants from air entering the electronic vaporizing device 100. The filtration element 128 may optionally comprise a fan 130 to assist in delivering air to the filtration element 128. The electronic vaporizing device 100 may be configured to intake air into the filtration element 128, filter the air, and pass the filtered air to the vaporizer 108 for use in vaporizing the one or more vaporizable or non-vaporizable materials. In another embodiment, the electronic vaporizing device 100 may be configured to intake air into the filtration element 128, filter the air, and bypass the vaporizer 108 by passing the filtered air directly to the outlet 114 for inhalation by a user.

In an embodiment, the filtration element 128 may comprise cotton, polymer, wool, satin, meta materials, and the like. The filtration element 128 may comprise a filter material that at least one airborne particle and/or undesired gas by a mechanical mechanism, an electrical mechanism, and/or a chemical mechanism. The filter material may comprise one or more pieces of a filter fabric that may filter out one or more airborne particles and/or gasses. The filter fabric may be a woven and/or non-woven material. The filter fabric may be made from natural fibers (e.g., cotton, wool, etc.) and/or from synthetic fibers (e.g., polyester, nylon, polypropylene, etc.). The thickness of the filter fabric may be varied depending on the desired filter efficiencies and/or the region of the apparel where the filter fabric is to be used. The filter fabric may be designed to filter airborne particles and/or gasses by mechanical mechanisms (e.g., weave density), by electrical mechanisms (e.g., charged fibers, charged metals, etc.), and/or by chemical mechanisms (e.g., absorptive charcoal particles, adsorptive materials, etc.). In as embodiment, the filter material may comprise electrically charged fibers such as, but not limited to, Filtrete® by 3M. In another embodiment, the filter material may comprise a high-density material similar to material used for medical masks which are used by medical personnel in doctors' offices, hospitals, and the like. In an embodiment, the filter material may be treated with an anti-bacterial solution and/or otherwise made from anti-bacterial materials. In another embodiment, the filtration element 128 may comprise electrostatic plates, ultraviolet light, a HEPA filter, combinations thereof, and the like.

In an embodiment, the electronic vaporizing device 100 may comprise a cooling element 132. The cooling element 132 may be configured to cool vapor exiting the vaporizer 108 prior to passing through the outlet 114. The cooling element 132 may cool vapor by utilizing air or space within the electronic vaporizing device 100. The air used by the cooling element 132 may be either static (existing in the electronic vaporizing device 100) or drawn into an intake and through the cooling element 132 and the electronic vaporizing device 100. The intake may comprise various pumping, pressure, fan, or other intake systems for drawing air into the cooling element 132. In an embodiment, the cooling element 132 may reside separately or may be integrated the vaporizer 108. The cooling element 132 may be a single cooled electronic element within a tube or space and/or the cooling element 132 may be configured as a series of coils or as a grid like structure. The materials for the cooling element 132 may be metal, liquid, polymer, natural substance, synthetic substance, air, or any combination thereof. The cooling element 132 may be powered by the power supply 120, by a separate battery (not shown), or other power source (not shown) including the use of excess heat energy created by the vaporizer 108 being converted to energy used for cooling by a small turbine or pressure system to convert the energy. Heat differentials between the vaporizer 108 and the cooling element 132 may also be converted to energy utilizing commonly known geothermal energy principles.

In an embodiment, the electronic vaporizing device 100 may comprise a magnetic element 134. For example, the magnetic element 134 may comprise an electromagnet, a ceramic magnet, a ferrite magnet, rare earth magnet, and/or the like. The magnetic element 134 may be configured to apply a magnetic field to air as it is brought into the electronic vaporizing device 100, in the vaporizer 108, and/or as vapor exits the outlet 114.

The input/output device 112 may be used to select whether vapor exiting the outlet 114 should be cooled or not cooled, heated or not heated, and/or magnetized or not magnetized. For example, a user may use the input/output device 112 to selectively cool vapor at times and not cool vapor at other times. The user may use the input/output device 112 to selectively heat vapor at times and not heat vapor at other times. The user may use the input/output device 112 to selectively magnetize vapor at times and not magnetize vapor at other times. The user may further use the input/output device 112 to select a desired smoothness, temperature, and/or range of temperatures. The user may adjust the temperature of the vapor by selecting or clicking on a clickable setting on a part of the electronic vaporizing device 100. The user may use, for example, a graphical user interface (GUI) or a mechanical input enabled by clicking a rotational mechanism at either end of the electronic vaporizing device 100.

In an embodiment, cooling control may be set within the electronic vaporizing device 100 settings via the processor 102 and system software (e.g., dynamic linked libraries). The memory 104 may store settings. Suggestions and remote settings may be communicated to and/or from the electronic vaporizing device 100 via the input/output device 112 and/or the network access device 106. Cooling of the vapor may be set and calibrated between heating and cooling mechanisms to what is deemed an ideal temperature by the manufacturer of the electronic vaporizing device 100 for the vaporizable material. For example, a temperature may be set such that resultant vapor delivers the coolest feeling to the average user but does not present any health risk to the user by the vapor being too cold, including the potential for rapid expansion of cooled vapor within the lungs and the damaging of tissue by vapor which has been cooled to a temperature which may cause frostbite-like symptoms.

In an embodiment, the electronic vaporizing device 100 may be configured to receive air, smoke, vapor or other material and analyze the contents of the air, smoke, vapor or other material using one or more sensors 136 to at least one of analyze, classify, compare, validate, refute, and/or catalogue the same. A result of the analysis may be, for example, an identification of at least one of medical, recreational, homeopathic, olfactory elements, spices, other cooking ingredients, ingredients analysis from food products, fuel analysis, pharmaceutical analysis, genetic modification testing analysis, dating, fossil and/or relic analysis and the like. The electronic vaporizing device 100 may utilize, for example, mass spectrometry, PH testing, genetic testing, particle and/or cellular testing, sensor based testing and other diagnostic and wellness testing, either via locally available components or by transmitting data to a remote system for analysis.

In an embodiment, a user may create a custom scent by using the electronic vaporizing device 100 to intake air elements, wherein the electronic vaporizing device 100 (or third-party networked device) analyzes the olfactory elements and/or biological elements within the sample. The electronic vaporizing device 100 and then formulates a replica scent within the electronic vaporizing device 100 (or third-party networked device) that may be accessed by the user instantly or at a later date, with the ability to purchase this custom scent from a networked ecommerce portal.

In another embodiment, the one or more sensors 136 may be configured to sense negative environmental conditions (e.g., adverse weather, smoke, fire, chemicals (e.g., such as $CO_2$ or formaldehyde), adverse pollution, and/or disease outbreaks, and the like). The one or more sensors 136 may comprise one or more of, a biochemical/chemical sensor, a thermal sensor, a radiation sensor, a mechanical sensor, an optical sensor, a mechanical sensor, a magnetic sensor, an electrical sensor, combinations thereof and the like. The biochemical/chemical sensor may be configured to detect one or more biochemical/chemicals causing a negative environmental condition such as, but not limited to, smoke, a vapor, a gas, a liquid, a solid, an odor, combinations thereof, and the like. The biochemical/chemical sensor may comprise one or more of a mass spectrometer, a conducting/nonconducting regions sensor, a SAW sensor, a quartz microbalance sensor, a conductive composite sensor, a chemiresistor, a metal oxide gas sensor, an organic gas sensor, a MOSFET, a piezoelectric device, an infrared sensor, a sintered metal oxide sensor, a Pd-gate MOSFET, a metal FET structure, an electrochemical cell, a conducting polymer sensor, a catalytic gas sensor, an organic semiconducting gas sensor, a solid electrolyte gas sensors, a piezoelectric quartz crystal sensor, and/or combinations thereof.

The thermal sensor may be configured to detect temperature, heat, heat flow, entropy, heat capacity, combinations thereof, and the like. Exemplary thermal sensors include, but are not limited to, thermocouples, such as semiconducting thermocouples, noise thermometry, thermoswitches, thermistors, metal thermoresistors, semiconducting thermoresistors, thermodiodes, thermotransistors, calorimeters, thermometers, indicators, and fiber optics.

The radiation sensor may be configured to detect gamma rays, X-rays, ultra-violet rays, visible, infrared, microwaves and radio waves. Exemplary radiation sensors are suitable for use in the present invention that include, but are not limited to, nuclear radiation microsensors, such as scintillation counters and solid state detectors; ultra-violet, visible and near infrared radiation microsensors, such as photoconductive cells; photodiodes; phototransistors; infrared radiation microsensors, such as photoconductive IR sensors; and pyroelectric sensors.

The optical sensor may be configured to detect visible, near infrared, and infrared waves. The mechanical sensor may be configured to detect displacement, velocity, acceleration, force, torque, pressure, mass, flow, acoustic wavelength, and amplitude. Exemplary mechanical sensors are suitable for use in the present invention and include, but are not limited to, displacement microsensors, capacitive and inductive displacement sensors, optical displacement sensors, ultrasonic displacement sensors, pyroelectric, velocity and flow microsensors, transistor flow microsensors, acceleration microsensors, piezoresistive microaccelerometers, force, pressure and strain microsensors, and piezoelectric crystal sensors. The magnetic sensor may be configured to detect magnetic field, flux, magnetic moment, magnetization, and magnetic permeability. The electrical sensor may be configured to detect charge, current, voltage, resistance, conductance, capacitance, inductance, dielectric permittivity, polarization and frequency.

Upon sensing a negative environmental condition, the one or more sensors 136 may provide data to the processor 102 to determine the nature of the negative environmental condition and to generate/transmit one or more alerts based on the negative environmental condition. The one or more alerts may be deployed to the electronic vaporizing device 100 user's wireless device and/or synced accounts. For example, the network device access device 106 may be used to transmit the one or more alerts directly (e.g., via Bluetooth®) to a user's smartphone to provide information to the user. In another embodiment, the network access device 106 may be used to transmit sensed information and/or the one or more alerts to a remote server for use in syncing one or more other devices used by the user (e.g., other vapor devices, other electronic devices (smartphones, tablets, laptops, etc.). In another embodiment, the one or more alerts may be provided to the user of the electronic vaporizing device 100 via vibrations, audio, colors, and the like deployed from the mask, for example through the input/output device 112. For example, the input/output device 112 may comprise a small vibrating motor to alert the user to one or more sensed conditions via tactile sensation. In another example, the input/output device 112 may comprise one or more LED's of various colors to provide visual information to the user. In another example, the input/output device 112 may comprise one or more speakers that may provide audio information to the user. For example, various patterns of beeps, sounds, and/or voice recordings may be utilized to provide the audio information to the user. In another example, the input/output device 112 may comprise an LCD screen/touchscreen that provides a summary and/or detailed information regarding the negative environmental condition and/or the one or more alerts.

In another embodiment, upon sensing a negative environmental condition, the one or more sensors 136 may provide data to the processor 102 to determine the nature of the negative environmental condition and to provide a recommendation for mitigating and/or to actively mitigate the negative environmental condition. Mitigating the negative environmental conditions may comprise, for example, applying a filtration system, a fan, a fire suppression system, engaging a HVAC system, and/or one or more vaporizable and/or non-vaporizable materials. The processor 102 may access a database stored in the memory device 104 to make such a determination or the network device 106 may be used to request information from a server to verify the sensor findings. In an embodiment, the server may provide an analysis service to the electronic vaporizing device 100. For example, the server may analyze data sent by the electronic vaporizing device 100 based on a reading from the one or more sensors 136. The server may determine and transmit one or more recommendations to the electronic vaporizing device 100 to mitigate the sensed negative environmental condition. The electronic vaporizing device 100 may use the one or more recommendations to activate a filtration system, a fan, a fire suppression system engaging a HVAC system, and/or to vaporize one or more vaporizable or non-vaporizable materials to assist in countering effects from the negative environmental condition.

In an embodiment, the electronic vaporizing device 100 may comprise a global positioning system (GPS) unit 118. The GPS unit 118 may detect a current location of the device 100. In some embodiments, a user may request access to one or more services that rely on a current location of the user. For example, the processor 102 may receive location data from the GPS 118, convert it to usable data, and transmit the usable data to the one or more services via the network access device 106. The GPS unit 118 may receive position information from a constellation of satellites operated by the U.S. Department of Defense. Alternately, the GPS unit 118 may be a GLONASS receiver operated by the Russian Federation Ministry of Defense, or any other positioning device capable of providing accurate location information (for example, LORAN, inertial navigation, and the like).

The GPS unit 118 may contain additional logic, either software, hardware or both to receive the Wide Area Augmentation System (WAAS) signals, operated by the Federal Aviation Administration, to correct dithering errors and provide the most accurate location possible. Overall accuracy of the positioning equipment subsystem containing WAAS is generally in the two-meter range.

In one embodiment, the electronic vaporizing device 100 may comprise at least one light-emitting element 142 coupled to the processor 102 to receive one or more control signals therefrom. The at least one light-emitting element 142 may be positioned on or near at least one of outlet 114 and outlet 124, and may be configured to illuminate in response to suction applied to at least one of outlet 114 and outlet 124. The illumination state and/or the intensity of illumination of the at least one light-emitting element 142 may be based on at least one of an amount of vaporizable material available, a vapor flow rate through at least one of outlet 114 and outlet 124, a direction of vapor flow, user preferences, and combinations thereof.

In one embodiment, the electronic vaporizing device 100 may operate in connection with an electronic communication device 150. The electronic communication device 150 may be integrated into device 100 or may be a separate device operatively coupled to device 100. As shown in FIG. 1B, the electronic communication device 150 may comprise a device processor 152 operable to control the operation of the electronic communication device 150. The device processor 152 may be, or may comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU), for example, one based on 80×86 architecture as designed by Intel™ or AMD™, or a system-on-a-chip as designed by ARM™.

The electronic communication device may further comprise a network access component 154 operatively coupled to the device processor 152 and configured to connect to at least one network 160. The network access component 154 may be operable to receive a plurality of electronic communications from the at least one network 160 via communication link 162. In a preferred embodiment, the network access component 154 may be operable to receive electronic communications in the form of least one of an instant message, a Short Message Service message, a Multimedia Messaging Service message, and an Enhanced Messaging Service message. At least one of the received electronic communications may include at least one command for controlling at least one operational parameter of the electronic vaporizing device 100. In one embodiment, the network access component 154 may be further operable to transmit the plurality of received electronic communications to the electronic vaporizing device 100.

The electronic communication device 150 may further comprise an input/output port 156 operatively coupled to the processor 102 of the electronic vaporizing device 100 and configured to transmit the plurality of communications to the electronic vaporizing device 100. The electronic communication device 150 may also comprise at least one power source 158 operatively connected to the device processor 152 and operable to generate a supply of power for operation of at least the electronic communication device 150.

In one embodiment, the device processor 152 may be operable to generate a plurality of electronic communications. In a preferred embodiment, device processor 152 may be operable to generate electronic communications in the form of at least one of an instant message, a Short Message Service message, a Multimedia Messaging Service message, and an Enhanced Messaging Service message. At least one of the generated electronic communications may include at least one command for controlling at least one operational parameter of the electronic vaporizing device 100. In one embodiment, at least a portion of the plurality of electronic communications may be generated by an associated user via a user interface associated with the electronic communication device 150.

In one embodiment, the network access component 154 may be further operable to transmit the plurality of generated electronic communications to at least one of the electronic vaporizing device 100 and the at least one network 160. For example, the device processor 152 may generate a text message, which may then be transmitted by the network access component 154 to the at least one network 160 for transmission to a remote device, such as another electronic vaporizing device, an electronic communication device, and the like.

In one embodiment, the processor 102 may be operable to generate a plurality of electronic communications. In a preferred embodiment, the processor 102 may be operable to generate electronic communications in the form of at least one of an instant message, a Short Message Service message, a Multimedia Messaging Service message, and an Enhanced Messaging Service message. In one embodiment, at least a portion of the plurality of electronic communications may be generated by an associated user via a user interface associated with the input/output device 112. In one embodiment, the input/output device 112 may be operable to transmit the plurality of generated electronic communications to the electronic communication device 150. For example, the processor 102 may generate a text message, which may then be transmitted by the input/output device 112 to the electronic communication device 150 for transmission to the at least one network 160. The text message may then be transmitted from the at least one network 160 to a remote device, such as another electronic vaporizing device, an electronic communication device, and the like.

In one embodiment, the input/output device 112 may be configured to receive a plurality of electronic communications from the electronic communication device 150. In a preferred embodiment, the input/output device 112 may be operable to receive electronic communications in the form of at least one of an instant message, a Short Message Service message, a Multimedia Messaging Service message, and an Enhanced Messaging Service message. At least one of the received electronic communications may include at least one command for controlling at least one operational parameter of the electronic vaporizing device 100. The input/output device 112 may be operable to transmit the at least one command to the processor 102 for controlling at least one operational parameter of the electronic vaporizing device 100.

In one embodiment, the processor 102 may be operable to generate at least one control signal for controlling at least one operational parameter of the electronic vaporizing device based on the at least one received command. In a preferred embodiment, the processor 102 may be operable to generate at least one mixing control signal for controlling at least one operational parameter of the mixing component 122 based on the at least one received command. The at least one command may include at least one of: an identification of the at least one container from which the selected amount of vaporizable material is withdrawn, the selected amount of vaporizable material withdrawn from the at least one container, timing of withdrawal of the material, rate of withdrawal of the material, and the like, and combinations thereof.

In one embodiment, the electronic vaporizing device 100 may comprise a plurality of containers 110, wherein each container may be configured to contain a vaporizable material or a constituent of a vaporizable material. It is to be understood that the one or more containers 110 may contain any suitable vaporizable material or constituent of a vaporizable material. The one or more containers 110 may be configured such that all the containers may store the same or similar vaporizable material, each of the containers may store a different, discrete vaporizable material, a select number of containers may store a first vaporizable material, a select number of containers may store a second vaporizable material, etc., and the like, and combinations thereof.

In a preferred embodiment, the processor 102 may be operable to generate at least one mixing control signal for controlling an amount of vaporizable material to be withdrawn from a selected number of the plurality of containers 110 by the mixing component 122 based on the at least one command. The at least one command may include at least one of an identification of each of a selected number of the plurality of containers from the vaporizable material is withdrawn, the selected amount of vaporizable material withdrawn from the selected number the plurality of containers, timing of withdrawal of the material, rate of withdrawal of the material, and the like, and combinations thereof.

In operation, the device processor 152 of the electronic communication device 150 may generate a plurality of electronic communications. In a preferred embodiment, the plurality of generated electronic communications may comprise at least one of an instant message, a Short Message Service message, a Multimedia Messaging Service message, and an Enhanced Messaging Service message. In one embodiment, at least one of the received communications may comprise at least one command for controlling at least one operational parameter of the electronic vaporizing device 100. The network access component 154 may then transmit the plurality of generated communications to the electronic vaporizing device 100. In one embodiment, at least a portion of the plurality of electronic communications may be generated by an associated user via a user interface associated with the electronic communication device 150.

In another embodiment, the network access component 154 may receive a plurality of electronic communications from the at least one network 160 via communication link 162. In a preferred embodiment, the plurality of received electronic communications may comprise at least one of an instant message, a Short Message Service message, a Multimedia Messaging Service message, and an Enhanced Messaging Service message. In one embodiment, at least one of the received communications may comprise at least one command for controlling at least one operational parameter of the electronic vaporizing device 100. The network access component 154 may then transmit the plurality of received communications to the electronic vaporizing device 100.

In operation, the input/output device 112 may receive the plurality of electronic communications transmitted by the network access component 154, including the at least one command for controlling at least one operational parameter of the electronic vaporizing device 100. The at least one command may then be transmitted to the processor 102, wherein the processor 102 may generate at least one control signal for controlling at least one operational parameter of the device 100 in accordance with the at least one command. In a preferred embodiment, the processor 102 may generate at least one mixing control signal for controlling the amount of vaporizable material to be withdrawn from the one or more containers 110 by the mixing component 122 in accordance with the at least one command. The mixing component 122 may then withdraw the specified amount of vaporizable material from the one or more containers 110 and provide the material to the vaporizer 108.

In one embodiment, the processor 102 may generate at least one mixing control signal for controlling an amount of vaporizable material to be withdrawn from a plurality of the containers 110 by the mixing component 122. The mixing component 122 may then withdraw the specified amount of vaporizable material from the each of the selected containers and provide the material to the vaporizer 108. At least a portion of the received vaporizable material may be vaporized by the vaporizer 108.

Figure 2:
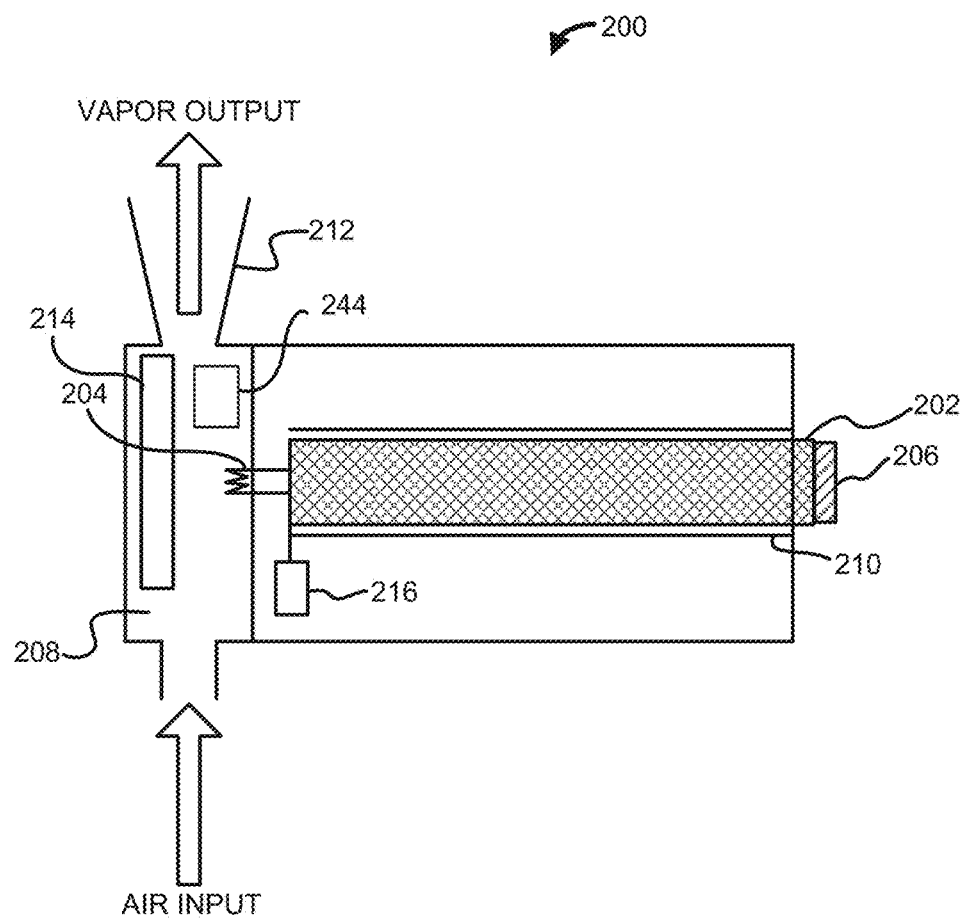
FIG. 2 is an illustration of one embodiment of an electronic vaporizing device according to some embodiments.

FIG. 2 illustrates one embodiment of an electronic vaporizer 200. The vaporizer 200 may be, for example, an e-cigarette, an e-cigar, an electronic vapor device, a hybrid electronic communication handset coupled/integrated vapor device, a robotic vapor device, a modified vapor device "mod," a micro-sized electronic vaporizing device, a robotic vapor device, and the like. The vaporizer 200 may be used internally of the electronic vaporizing device 100 or may be a separate device. For example, the vaporizer 200 may be used in place of the vaporizer 108.

Figure 14:
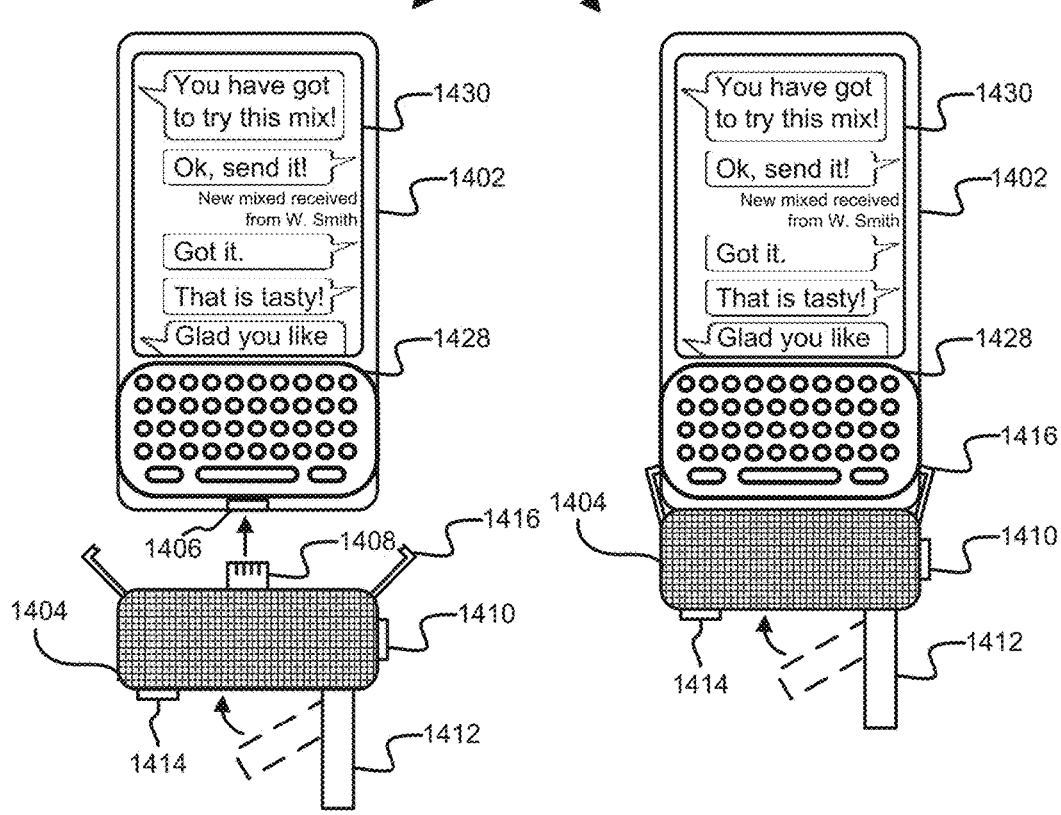
FIGS. 14a, 14b, and 14c illustrate one embodiment of an electronic vaporizing device according to some embodiments.

In one embodiment, the vaporizer 200 may be coupled to an electronic communication device. The electronic communication device may be one or more of a smart watch (and any other form of "smart" wearable technology), a smartphone, a tablet, a laptop, a desktop, and the like. In one embodiment, the electronic communication device may be capable of communicating with other devices via only messages, such as text message, (e.g., no telephone capabilities). In one embodiment, the vaporizer 200 may be coupled to the electronic communication device using a shuttle form factor. The shuttle form factor may be any suitable size and/or shape sufficient to be coupled to the electronic communication device. For example, the vaporizer 200 having a shuttle form factor may be coupled to the electronic communication device via at least one of a USB connection, a dock connector (e.g., 20-40-30 pin connectors, lightening port connection, etc.), Portable Digital Media Interface, and the like. FIGS. 14A, 14B, and 14C illustrate an example vaporizer in the shuttle form factor.

The vaporizer 200 may comprise or be coupled to one or more containers 202 containing a vaporizable material, for example a fluid. For example, coupling between the vaporizer 200 and the one or more containers 202 may be via a wick 204, a valve, or by some other coupling/engagement structure. Coupling may operate independently of gravity, such as by capillary action or pressure drop through a valve. The vaporizer 200 may be configured to vaporize the vaporizable material from the one or more containers 202 at controlled rates in response to mechanical input from a component of the electronic vaporizing device 100, and/or in response to control signals from the processor 102 or another component. Vaporizable material (e.g., fluid) may be supplied by one or more replaceable cartridges 206. In an embodiment, the vaporizable material may comprise aromatics and/or aromatic elements. In an embodiment, the aromatic elements may be medicinal, recreational, therapeutic, and/or wellness related. The aromatic element may include, but is not limited to, at least one of lavender or other floral aromatic eLiquids, mint, menthol, herbal, extracts, soil or geologic, plant based, name brand perfumes, custom mixed perfume formulated inside the electronic vaporizing device 100 and aromas constructed to replicate the smell of different geographic places, conditions, and/or occurrences. For example, the smell of places may include specific or general sports venues, well known travel destinations, the mix of one's own personal space or home. The smell of conditions may include, for example, the smell of a pet, a baby, a season, a general environment (e.g., a forest), a new car, a sexual nature (e.g., musk, pheromones, etc.). The one or more replaceable cartridges 206 may contain the vaporizable material. If the vaporizable material is liquid, the cartridge may comprise the wick 204 to aid in transporting the liquid to a mixing chamber 208. In the alternative, some other transport mode may be used. Each of the one or more replaceable cartridges 206 may be configured to fit inside and engage removably with a receptacle (such as the container 202 and/or a secondary container) of the electronic vaporizing device 100. In an alternative, or in addition, one or more fluid containers 210 may be fixed in the electronic vaporizing device 100 and configured to be refillable. In an embodiment, one or more materials may be vaporized at a single time by the vaporizer 200. For example, some material may be vaporized and drawn through an exhaust port 212 and/or some material may be vaporized and exhausted via a smoke simulator outlet (not shown).

The mixing chamber 208 may also receive one or more compounds or materials to be vaporized. For example, the processor 102 may determine a first amount of a first compound to be withdrawn and a second amount of a second compound to be withdrawn. The processor 102 may then generate a control signal for the first amount of the first compound to be withdrawn from a first container and the second amount of the second amount to be withdrawn from a second container.

In another embodiment, the processor 102 may further be operable to determine a target dose of the first compound, determine a vaporization ratio of the first compound and the second compound based on the target dose, determine a first amount of the first compound to be withdrawn based on the vaporization ratio, and determine a second amount of the second compound to be withdrawn based on the vaporization ratio. The processor 102 may then generate a control signal for the first amount of the first compound to be withdrawn from a first container and the second amount of the second amount to be withdrawn from a second container. After the vapor is generated and expelled through an exhaust port for inhalation by the user, the processor 102 may also be operable to determine that a cumulative dose is approaching the target dose. The processor 102 may then generate a control signal to reduce the vaporization ratio. It is to be understood that the determination of the vaporization ratio, the target dose, and/or the cumulative dose may be determined remotely by an associated electronic communication device. The processor 102 may then generate a control signal. The processor 102 may then generate a control signal and transmitted to the electronic vaporizing device 100 for use.

In operation, a heating element 214 may vaporize or nebulize the vaporizable material in the mixing chamber 208, producing an inhalable vapor/mist that may be expelled via the exhaust port 212. In an embodiment, the heating element 214 may comprise a heater coupled to the wick (or a heated wick) 204 operatively coupled to (for example, in fluid communication with) the mixing chamber 210. The heating element 214 may comprise a nickel-chromium wire or the like, with a temperature sensor (not shown) such as a thermistor or thermocouple. Within definable limits, by controlling power to the wick 204, a rate of vaporization may be independently controlled. Multiplexers 208 and 216 may receive power from a vaporizer power supply 218 and/or from a power supply 120 built into the electronic vaporizing device 100. At a minimum, control may be provided between no power (off state) and one or more powered states. Other control mechanisms may also be suitable.

In another embodiment, the vaporizer 200 may comprise a piezoelectric dispersing element 244. In some embodiments, the piezoelectric dispersing element 244 may be charged by a battery, and may be driven by a processor on a circuit board. The circuit board may be produced using a polyimide such as Kapton®, or other suitable material. The piezoelectric dispersing element 244 may comprise a thin metal disc which causes dispersion of the fluid fed into the dispersing element via the wick or other soaked piece of organic material through vibration. Once in contact with the piezoelectric dispersing element, the vaporizable material (e.g., fluid) may be vaporized (e.g., turned into vapor or mist) and the vapor may be dispersed via a system pump and/or a sucking action of the user. In some embodiments, the piezoelectric dispersing element 244 may cause dispersion of the vaporizable material by producing ultrasonic vibrations. An electric field applied to a piezoelectric material within the piezoelectric element may cause ultrasonic expansion and contraction of the piezoelectric material, resulting in ultrasonic vibrations to the disc. The ultrasonic vibrations may cause the vaporizable material to disperse, thus forming a vapor or mist from the vaporizable material.

In an embodiment, the vaporizer 200 may be configured to permit a user to select between using the heating element 214 or the piezoelectric dispersing element 244. In another embodiment, the vaporizer 200 may be configured to permit a user to utilize both the heating element 214 and the piezoelectric dispersing element 244.

In some embodiments, the connection between a power supply and the piezoelectric dispersing element 244 may be facilitated using one or more conductive coils. The conductive coils may provide an ultrasonic power input to the piezoelectric dispersing element 244. For example, the signal carried by the coil may have a frequency of approximately 107.8 kHz. In some embodiments, the piezoelectric dispersing element 244 may comprise a piezoelectric dispersing element that may receive the ultrasonic signal transmitted from the power supply through the coils, and may cause vaporization of the vaporizable liquid by producing ultrasonic vibrations. An ultrasonic electric field applied to a piezoelectric material within the piezoelectric dispersing element 244 causes ultrasonic expansion and contraction of the piezoelectric material, resulting in ultrasonic vibrations according to the frequency of the signal. The vaporizable liquid may be vibrated by the ultrasonic energy produced by the piezoelectric dispersing element 244, thus causing dispersal and/or atomization of the liquid.

Figure 3:
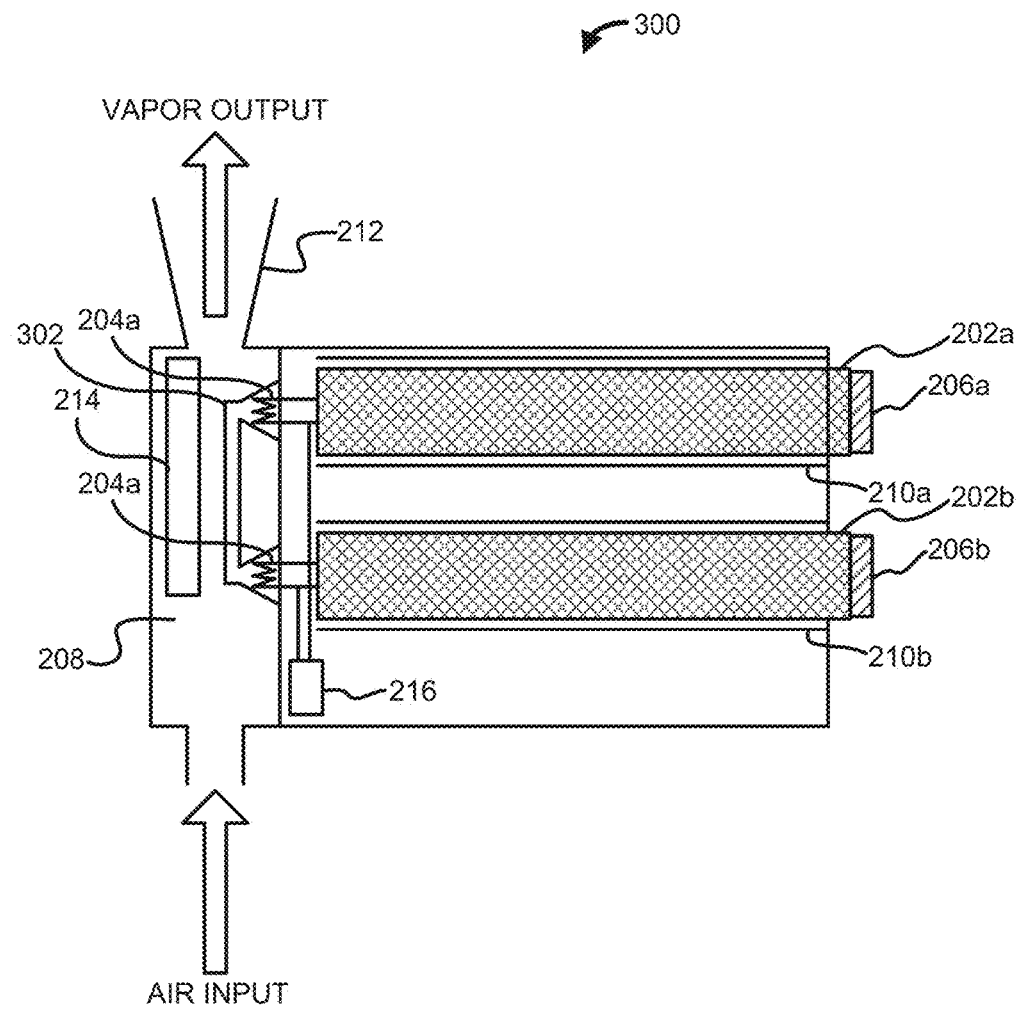
FIG. 3 is an illustration of one embodiment of an electronic vaporizing device configured for vaporizing a mixture of vaporizable material according to some embodiments.

FIG. 3 illustrates one embodiment of a vaporizer 300 that comprises the elements of the vaporizer 200 with two containers 202a and 202b containing a vaporizable material, for example a fluid. In an embodiment, the fluid may be the same fluid in both containers or the fluid may be different in each container. In an embodiment, the fluid may comprise aromatic elements. The aromatic element may include, but is not limited to, at least one of lavender or other floral aromatic eLiquids, mint, menthol, herbal soil or geologic, plant based, name brand perfumes, custom mixed perfume formulated inside the electronic vaporizing device 100 and aromas constructed to replicate the smell of different geographic places, conditions, and/or occurrences. For example, the smell of places may include specific or general sports venues, well known travel destinations, the mix of one's own personal space or home. The smell of conditions may include, for example, the smell of a pet, a baby, a season, a general environment (e.g., a forest), a new car, a sexual nature (e.g., musk, pheromones, etc.). Coupling between the vaporizer 200 and the container 202a and the container 202b may be via a wick 204a and a wick 204b, respectively, via a valve, or by some other structure. Coupling may operate independently of gravity, such as by capillary action or pressure drop through a valve. The vaporizer 300 may be configured to mix in varying proportions the fluids contained in the container 202a and the container 202b and vaporize the mixture at controlled rates in response to mechanical input from a component of the electronic vaporizing device 100, and/or in response to control signals from the processor 102 or another component. In an embodiment, a mixing element 302 may be coupled to the container 202a and the container 202b. The mixing element may, in response to a control signal from the processor 102, withdraw select quantities of vaporizable material to create a customized mixture of different types of vaporizable material. Vaporizable material (e.g., fluid) may be supplied by one or more replaceable cartridges 206a and 206b. The one or more replaceable cartridges 206a and 206b may contain a vaporizable material. If the vaporizable material is liquid, the cartridge may comprise the wick 204a or 204b to aid in transporting the liquid to a mixing chamber 208. In the alternative, some other transport mode may be used. Each of the one or more replaceable cartridges 206a and 206b may be configured to fit inside and engage removably with a receptacle (such as the container 202a or the container 202b and/or a secondary container) of the electronic vaporizing device 100. In an alternative, or in addition, one or more fluid containers 210a and 210b may be fixed in the electronic vaporizing device 100 and configured to be refillable. In an embodiment, one or more materials may be vaporized at a single time by the vaporizer 300. For example, some material may be vaporized and drawn through an exhaust port 212 and/or some material may be vaporized and exhausted via a smoke simulator outlet (not shown).

Figure 4:
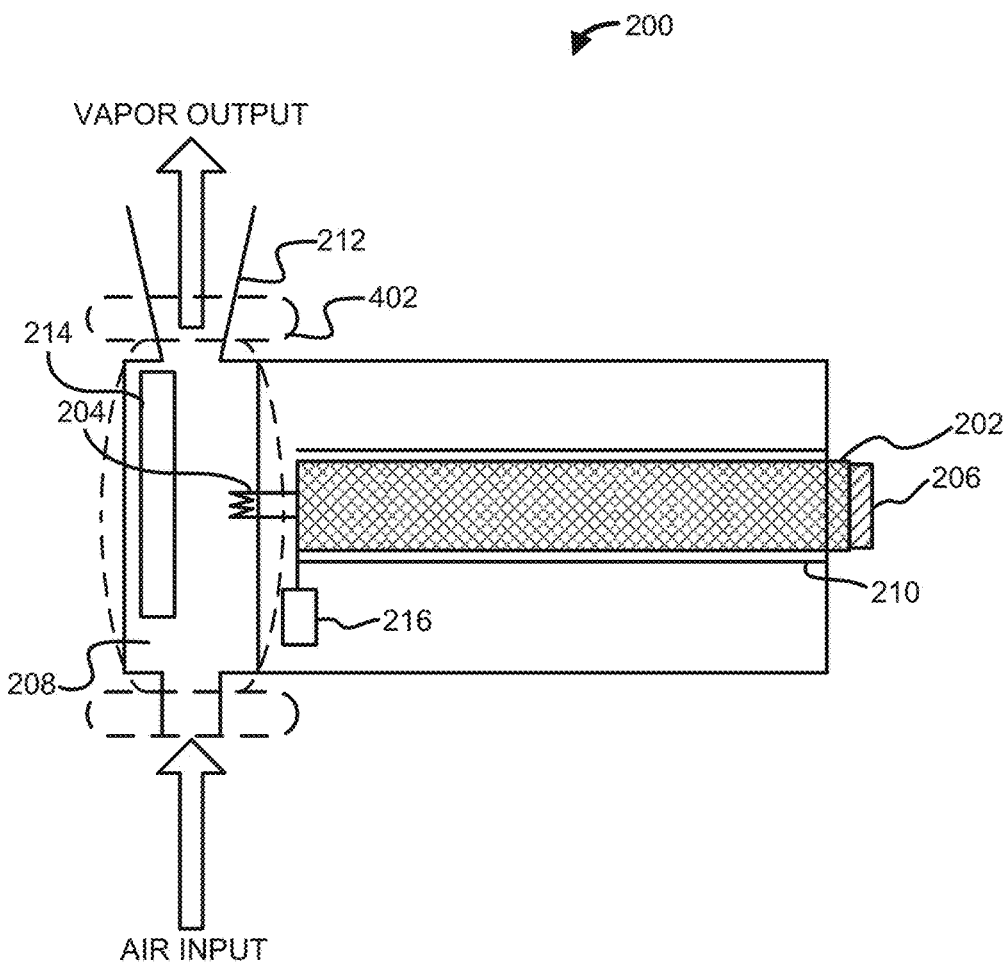
FIG. 4 is an illustration of one embodiment of an electronic vaporizing device configured for smooth vapor delivery according to some embodiments.

FIG. 4 illustrates one embodiment of a vaporizer 200 that comprises the elements of the vaporizer 200 with a heating casing 402. The heating casing 402 may enclose the heating element 214 or may be adjacent to the heating element 214. The heating casing 402 is illustrated with dashed lines, indicating components contained therein. The heating casing 402 may preferably be made of ceramic, metal, and/or porcelain. The heating casing 402 may have varying thickness. In an embodiment, the heating casing 402 may be coupled to the multiplexer 216 to receive power to heat the heating casing 402. In another embodiment, the heating casing 402 may be coupled to the heating element 214 to heat the heating casing 402. In another embodiment, the heating casing 402 may serve as an insulator.

Figure 5:
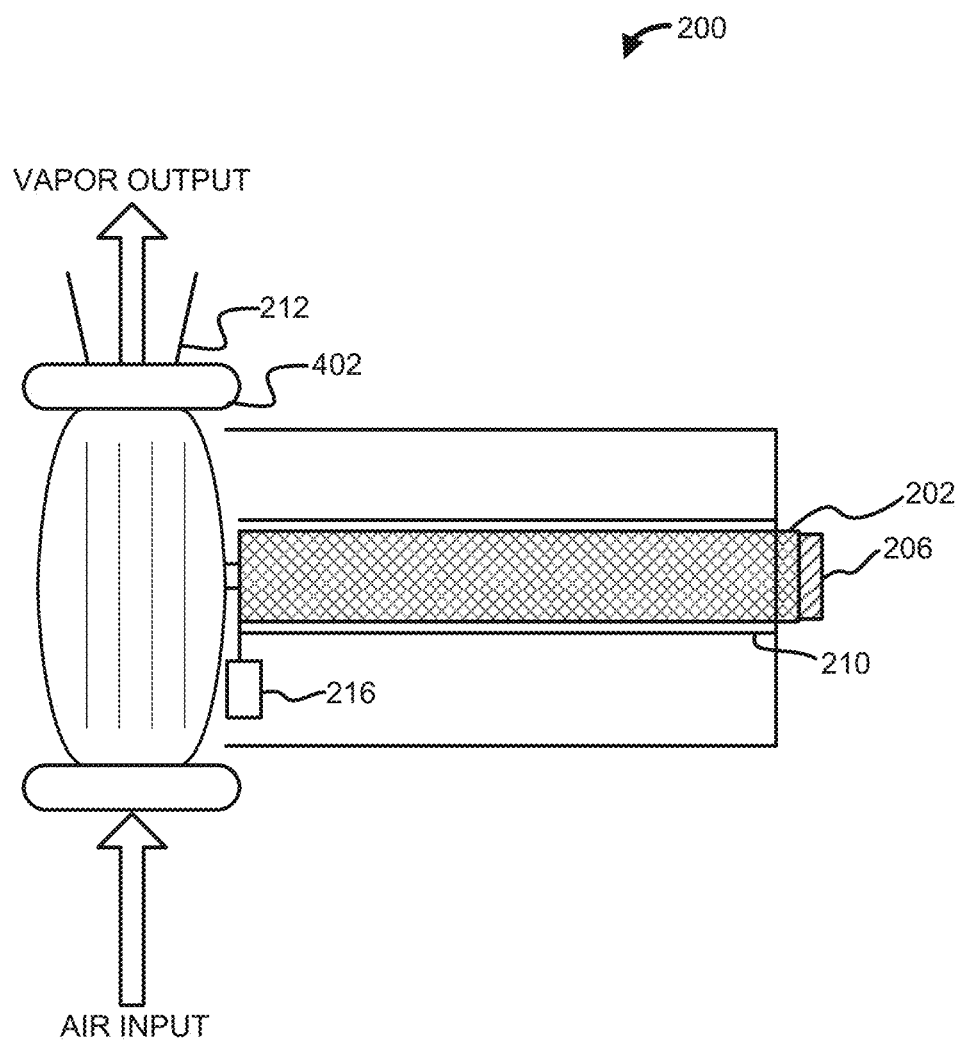
FIG. 5 is an illustration of one embodiment of an electronic vaporizing device configured for smooth vapor delivery according to some embodiments.

FIG. 5 illustrates one embodiment of the vaporizer 200 of FIG. 4, but illustrates the heating casing 402 with solid lines, indicating components contained therein. Other placements of the heating casing 402 are contemplated. For example, the heating casing 402 may be placed after the heating element 214 and/or the mixing chamber 208.

Figure 6:
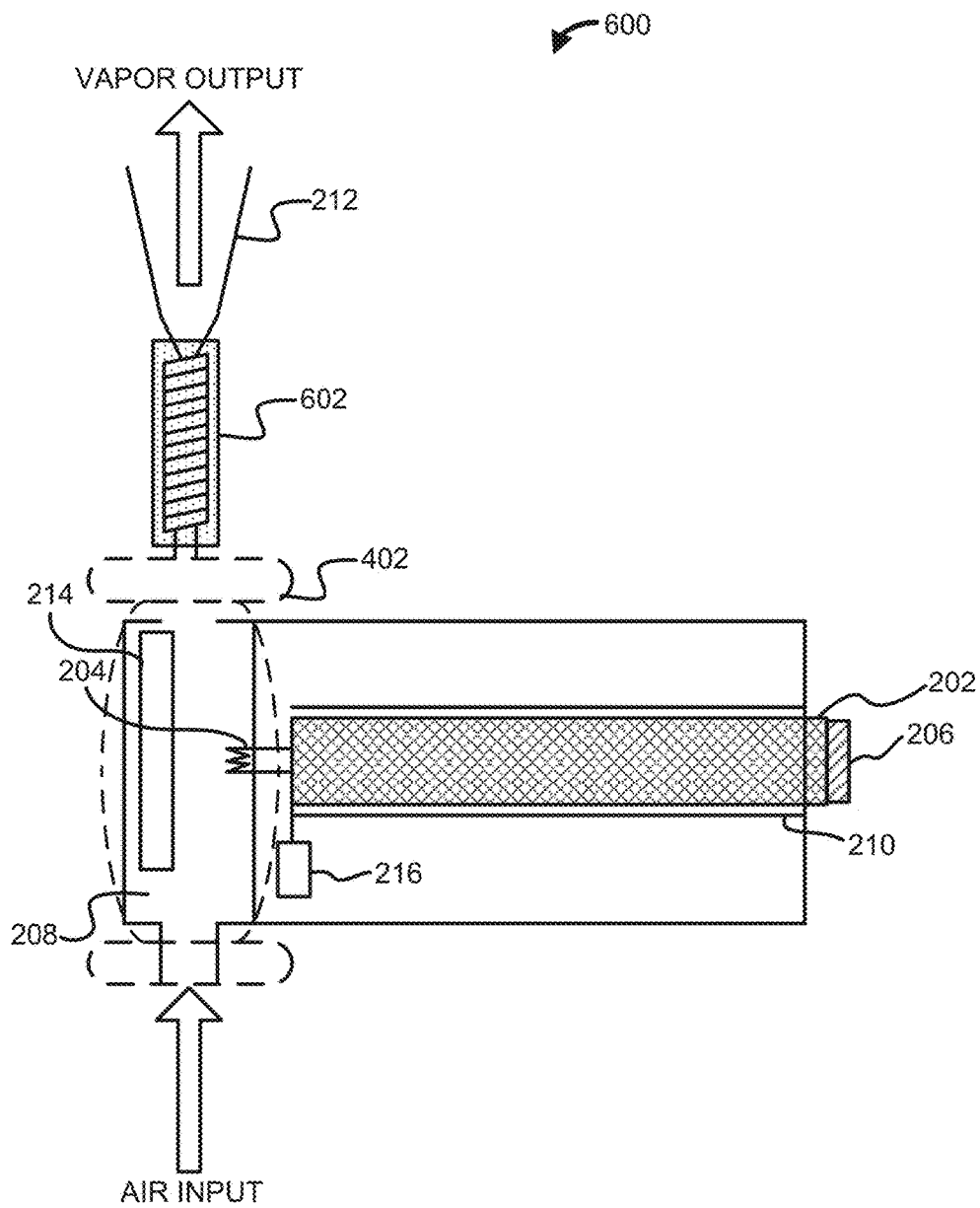
FIG. 6 is an illustration of one embodiment of an electronic vaporizing device configured for smooth vapor delivery according to some embodiments.

FIG. 6 illustrates one embodiment of a vaporizer 600 that comprises the elements of the vaporizer 200 of FIG. 2 and FIG. 4, with the addition of a cooling element 602. The vaporizer 600 may optionally comprise the heating casing 402. The cooling element 602 may comprise one or more of a powered cooling element, a cooling air system, and/or or a cooling fluid system. The cooling element 602 may be self-powered, co-powered, or directly powered by a battery and/or charging system within the electronic vaporizing device 100 (e.g., the power supply 120). In an embodiment, the cooling element 602 may comprise an electrically connected conductive coil, grating, and/or other design to efficiently distribute cooling to the vaporized and/or non-vaporized air. For example, the cooling element 602 may be configured to cool air as it is brought into the vaporizer 600/mixing chamber 208 and/or to cool vapor after it exits the mixing chamber 208. The cooling element 602 may be deployed such that the cooling element 602 is surrounded by the heated casing 402 and/or the heating element 214. In another embodiment, the heated casing 402 and/or the heating element 214 may be surrounded by the cooling element 602. The cooling element 602 may utilize at least one of cooled air, cooled liquid, and/or cooled matter.

In an embodiment, the cooling element 602 may be a coil of any suitable length and may reside proximate to the inhalation point of the vapor (e.g., the exhaust port 212). The temperature of the air is reduced as it travels through the cooling element 602. In an embodiment, the cooling element 602 may comprise any structure that accomplishes a cooling effect. For example, the cooling element 602 may be replaced with a screen with a mesh or grid-like structure, a conical structure, and/or a series of cooling airlocks, either stationary or opening, in a periscopic/telescopic manner. The cooling element 602 may be any shape and/or may take multiple forms capable of cooling heated air, which passes through its space.

In an embodiment, the cooling element 602 may be any suitable cooling system for use in a vapor device. For example, a fan, a heat sink, a liquid cooling system, a chemical cooling system, combinations thereof, and the like. In an embodiment, the cooling element 602 may comprise a liquid cooling system whereby a fluid (e.g., water, coolant) passes through pipes in the vaporizer 600. As this fluid passes around the cooling element 602, the fluid absorbs heat, cooling the air in the cooling element 602. After the fluid absorbs the heat, the fluid may pass through a heat exchanger which transfers the heat from the fluid to air blowing through the heat exchanger. By way of further example, the cooling element 602 may comprise a chemical cooling system that utilizes an endothermic reaction. An example of an endothermic reaction is dissolving ammonium nitrate in water. Such endothermic process is used in instant cold packs. These cold packs have a strong outer plastic layer that holds a bag of water and a chemical, or mixture of chemicals, that result in an endothermic reaction when dissolved in water. When the cold pack is squeezed, the inner bag of water breaks and the water mixes with the chemicals. The cold pack starts to cool as soon as the inner bag is broken, and stays cold for over an hour. Many instant cold packs contain ammonium nitrate. When ammonium nitrate is dissolved in water, it splits into positive ammonium ions and negative nitrate ions. In the process of dissolving, the water molecules contribute energy, and as a result, the water cools down. Thus, the vaporizer 600 may comprise a chamber for receiving the cooling element 602 in the form of a "cold pack." The cold pack may be activated prior to insertion into the vaporizer 600 or may be activated after insertion through use of a button/switch and the like to mechanically activate the cold pack inside the vaporizer 600.

In an embodiment, the cooling element 602 may be selectively moved within the vaporizer 600 to control the temperature of the air mixing with vapor. For example, the cooling element 602 may be moved closer to the exhaust port 212 or further from the exhaust port 212 to regulate temperature. In another embodiment, insulation may be incorporated as needed to maintain the integrity of heating and cooling, as well as absorbing any unwanted condensation due to internal or external conditions, or a combination thereof. The insulation may also be selectively moved within the vaporizer 600 to control the temperature of the air mixing with vapor. For example, the insulation may be moved to cover a portion, none, or all of the cooling element 602 to regulate temperature.

Figure 7:
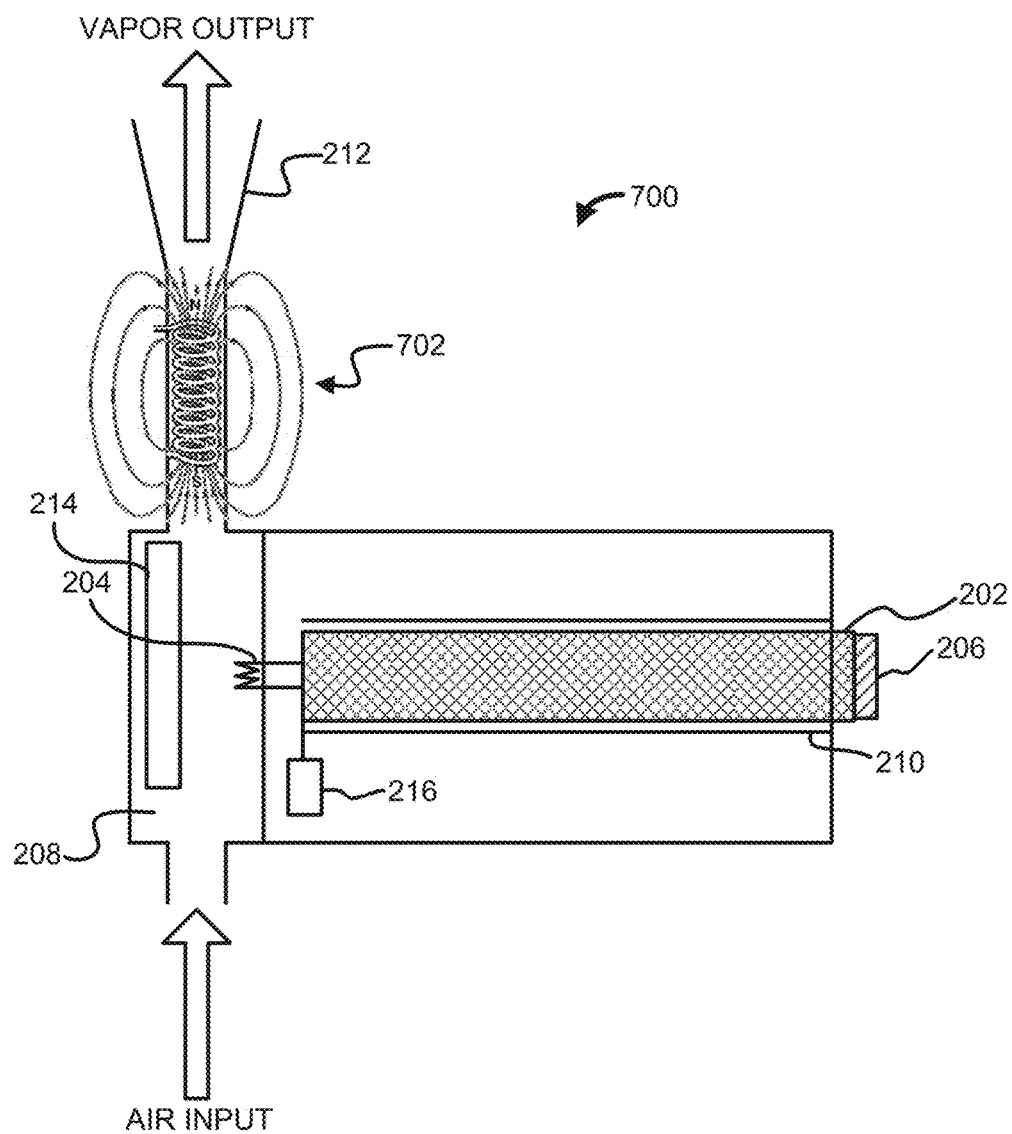
FIG. 7 is an illustration of one embodiment of an electronic vaporizing device configured for smooth vapor delivery according to some embodiments.

FIG. 7 illustrates one embodiment of a vaporizer 700 that comprises elements in common with the vaporizer 200. The vaporizer 700 may optionally comprise a heating casing (not shown) and/or cooling element (not shown) as discussed above. The vaporizer 700 may comprise a magnetic element 702. The magnetic element 702 may apply a magnetic field to vapor after exiting the mixing chamber 208. The magnetic field may cause positively and negatively charged particles in the vapor to curve in opposite directions, according to the Lorentz force law with two particles of opposite charge. The magnetic field may be created by at least one of an electric current generating a charge or a pre-charged magnetic material deployed within the electronic vaporizing device 100. In an embodiment, the magnetic element 702 may be built into the mixing chamber 208, the cooling element 602, the heating casing 402, or may be a separate magnetic element 702.

Figure 8:
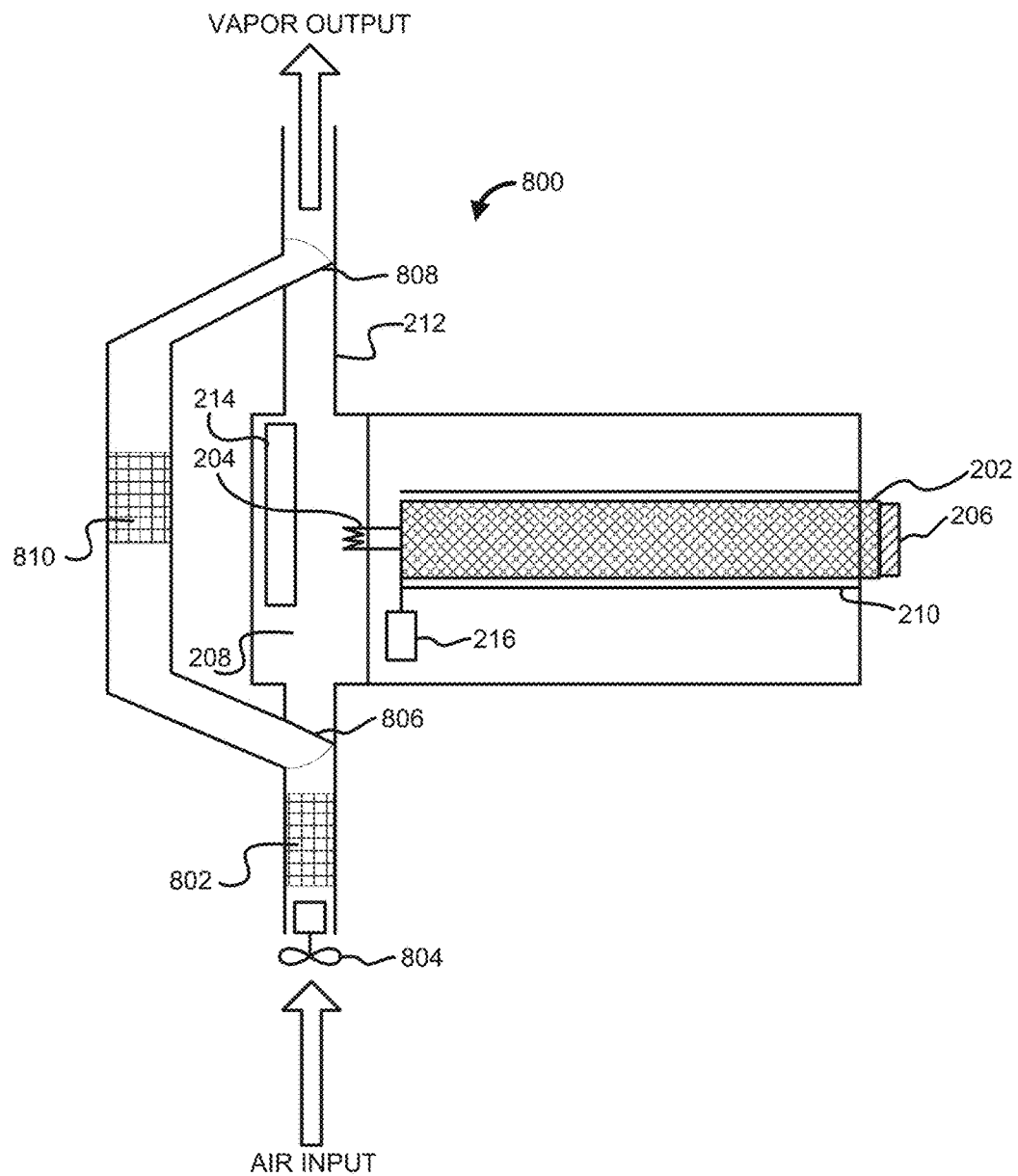
FIG. 8 is an illustration of one embodiment of an electronic vaporizing device configured for filtering air according to some embodiments.

FIG. 8 illustrates one embodiment of a vaporizer 800 that comprises elements in common with the vaporizer 200. In an embodiment, the vaporizer 800 may comprise a filtration element 802. The filtration element 802 may be configured to remove (e.g., filter, purify, etc.) contaminants from air entering the vaporizer 800. The filtration element 802 may optionally comprise a fan 804 to assist in delivering air to the filtration element 802. The vaporizer 800 may be configured to intake air into the filtration element 802, filter the air, and pass the filtered air to the mixing chamber 208 for use in vaporizing the one or more vaporizable or non-vaporizable materials. In another embodiment, the vaporizer 800 may be configured to intake air into the filtration element 802, filter the air, and bypass the mixing chamber 208 by engaging a door 806 and a door 808 to pass the filtered air directly to the exhaust port 212 for inhalation by a user. In an embodiment, filtered air that bypasses the mixing chamber 208 by engaging the door 806 and the door 808 may pass through a second filtration element 810 to further remove (e.g., filter, purify, etc.) contaminants from air entering the vaporizer 800. In an embodiment, the vaporizer 800 may be configured to deploy and/or mix a proper/safe amount of oxygen which may be delivered either via the one or more replaceable cartridges 206 or via air pumped into a mask from external air and filtered through the filtration element 802 and/or the filtration element 810.

In an embodiment, the filtration element 802 and/or the filtration element 810 may comprise cotton, polymer, wool, satin, meta materials and the like. The filtration element 802 and/or the filtration element 810 may comprise a filter material that at least one airborne particle and/or undesired gas by a mechanical mechanism, an electrical mechanism, and/or a chemical mechanism. The filter material may comprise one or more pieces of, a filter fabric that may filter out one or more airborne particles and/or gasses. The filter fabric may be a woven and/or non-woven material. The filter fabric may be made from natural fibers (e.g., cotton, wool, etc.) and/or from synthetic fibers (e.g., polyester, nylon, polypropylene, etc.). The thickness of the filter fabric may be varied depending on the desired filter efficiencies and/or the region of the apparel where the filter fabric is to be used. The filter fabric may be designed to filter airborne particles and/or gasses by mechanical mechanisms (e.g., weave density), by electrical mechanisms (e.g., charged fibers, charged metals, etc.), and/or by chemical mechanisms (e.g., absorptive charcoal particles, adsorptive materials, etc.). In as embodiment, the filter material may comprise electrically charged fibers such as, but not limited to, Filtrete® by 3M. In another embodiment, the filter material may comprise a high-density material similar to material used for medical masks which are used by medical personnel in doctors' offices, hospitals, and the like. In an embodiment, the filter material may be treated with an anti-bacterial solution and/or otherwise made from anti-bacterial materials. In another embodiment, the filtration element 802 and/or the filtration element 810 may comprise electrostatic plates, ultraviolet light, a HEPA filter, combinations thereof, and the like.

Figure 9:
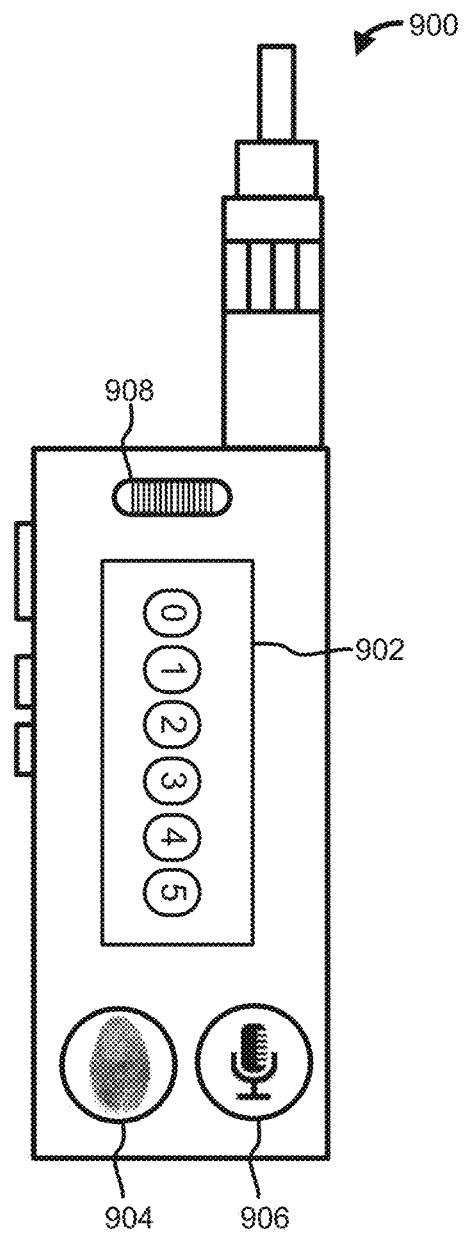
FIG. 9 illustrates one embodiment of an interface for an electronic vaporizing device according to some embodiments.

FIG. 9 illustrates one embodiment of a vapor device 900. The exemplary vapor device 900 may comprise the electronic vaporizing device 100 and/or any of the vaporizers 200, 600, 700, 800 disclosed herein. The vapor device 900 illustrates a display 902. The display 902 may be a touch-screen. The display 902 may be configured to enable a user to control any and/or all functionality of the vapor device 900. For example, a user may utilize the display 902 to enter a pass code to lock and/or unlock the vapor device 900. The vapor device 900 may comprise a biometric interface 904. For example, the biometric interface 904 may comprise a fingerprint scanner, an eye scanner, a facial scanner, and the like. The biometric interface 904 may be configured to enable a user to control any and/or all functionality of the vapor device 900. The vapor device 900 may comprise an audio interface 906. The audio interface 906 may comprise a button that, when engaged, enables a microphone 908. The microphone 908 may receive audio signals and provide the audio signals to a processor for interpretation into one or more commands to control one or more functions of the vapor device 900.

Figure 10:
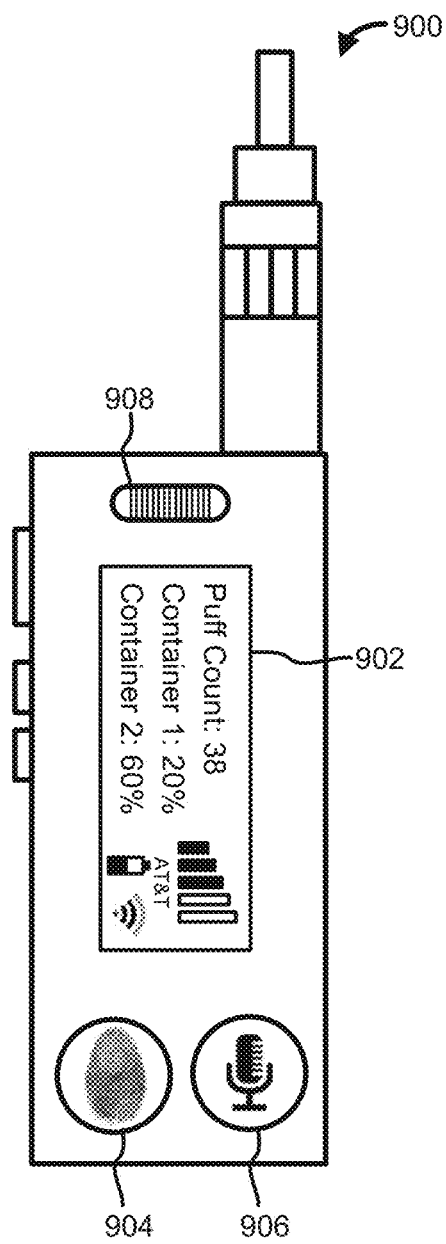
FIG. 10 illustrates one embodiment of an interface for an electronic vaporizing device according to some embodiments.

FIG. 10 illustrates one embodiment of exemplary information that may be provided to a user via the display 902 of the vapor device 900. The display 902 may provide information to a power remaining in one or more power supplied, signal strength, combinations thereof, and the like. The display 902 is preferably digital, but may be analog.

Figure 11:
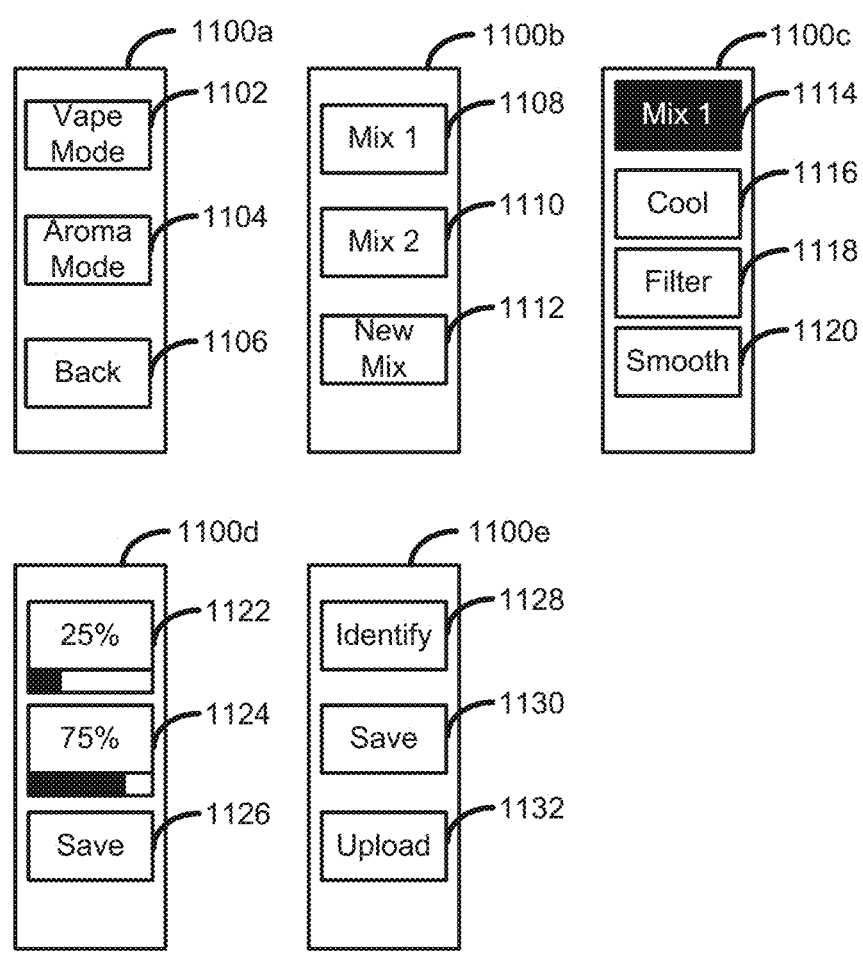
FIG. 11 are diagrams that illustrate several embodiments of an interface for an electronic vaporizing device according to some embodiments.

FIG. 11 illustrates a series of user interfaces that may be provided via the display 902 of the vapor device 900. In an embodiment, the exemplary vapor device 900 may be configured for one or more of multi-mode vapor usage. For example, the exemplary vapor device 900 may be configured to enable a user to inhale vapor (vape mode) or to release vapor into the atmosphere (aroma mode). User interface 1100a provides a user with interface elements to select which mode the user wishes to engage, a Vape Mode 1102, an Aroma Mode 1104, or an option to go back 1106 and return to the previous screen. The interface element Vape Mode 1102 enables a user to engage a vaporizer to generate a vapor for inhalation. The interface element Aroma Mode 1104 enables a user to engage the vaporizer to generate a vapor for release into the atmosphere.

In the event a user selects the Vape Mode 1102, the exemplary vapor device 900 will be configured to vaporize material and provide the resulting vapor to the user for inhalation. The user may be presented with user interface 1100b which provides the user an option to select interface elements that will determine which vaporizable material to vaporize. For example, an option of Mix 1 1108, Mix 2 1110, or a New Mix 1112. The interface element Mix 1 1108 enables a user to engage one or more containers that contain vaporizable material in a predefined amount and/or ratio. In an embodiment, a selection of Mix 1 1108 may result in the exemplary vapor device 900 engaging a single container containing a single type of vaporizable material or engaging a plurality of containers containing different types of vaporizable material in varying amounts. The interface element Mix 2 1110 enables a user to engage one or more containers that contain vaporizable material in a predefined amount and/or ratio. In an embodiment, a selection of Mix 2 1110 may result in the exemplary vapor device 900 engaging a single container containing a single type of vaporizable material or engaging a plurality of containers containing different types of vaporizable material in varying amounts. In an embodiment, a selection of New Mix 1112 may result in the exemplary vapor device 900 receiving a new mixture, formula, recipe, etc., of vaporizable materials and/or engage one or more containers that contain vaporizable material in the new mixture.

Upon selecting, for example, the Mix 1 1108, the user may be presented with user interface 1100c. User interface 1100c indicates to the user that Mix 1 has been selected via an indicator 1114. The user may be presented with options that control how the user wishes to experience the selected vapor. The user may be presented with interface elements Cool 1116, Filter 1118, and Smooth 1120. The interface element Cool 1116 enables a user to engage one or more cooling elements to reduce the temperature of the vapor. The interface element Filter 1118 enables a user to engage one or more filter elements to filter the air used in the vaporization process. The interface element Smooth 1120 enables a user to engage one or more heating casings, cooling elements, filter elements, and/or magnetic elements to provide the user with a smoother vaping experience.

Upon selecting New Mix 1112, the user may be presented with user interface 1100d. User interface 1100d provides the user with a container one ratio interface element 1122, a container two ratio interface element 1124, and Save 1126. The container one ratio interface element 1122 and the container two ratio interface element 1124 provide a user the ability to select an amount of each type of vaporizable material contained in container one and/or container two to utilize as a new mix. The container one ratio interface element 1122 and the container two ratio interface element 1124 may provide a user with a slider that adjusts the percentages of each type of vaporizable material based on the user dragging the slider. In an embodiment, a mix may comprise 100% on one type of vaporizable material or any percent combination (e.g., 50/50, 75/25, 85/15, 95/5, etc.). Once the user is satisfied with the new mix, the user may select Save 1126 to save the new mix for later use.

In the event a user selects the Aroma Mode 1104, the exemplary vapor device 900 may be configured to vaporize the material and release the resulting vapor into the atmosphere. The user may be presented with user interface 1100b, 1100c, and/or 1100d as described above, but the vapor will be released to the atmosphere.

In an embodiment, the user may be presented with user interface 1100e. The user interface 1100e may provide the user with interface elements Identify 1128, Save 1130, and Upload 1132. The interface element Identify 1128 enables a user to engage one or more sensors in the exemplary vapor device 900 to analyze the surrounding environment. For example, activating the interface element Identify 1128 may engage a sensor to determine the presence of a negative environmental condition such as smoke, a bad smell, chemicals, etc. Activating the interface element Identify 1128 may engage a sensor to determine the presence of a positive environmental condition, for example, an aroma. The interface element Save 1130 enables a user to save data related to the analyzed negative and/or positive environmental condition in memory local to the exemplary vapor device 900. The interface element Upload 1132 enables a user to engage a network access device to transmit data related to the analyzed negative and/or positive environmental condition to a remote server for storage and/or analysis.

Figure 12:
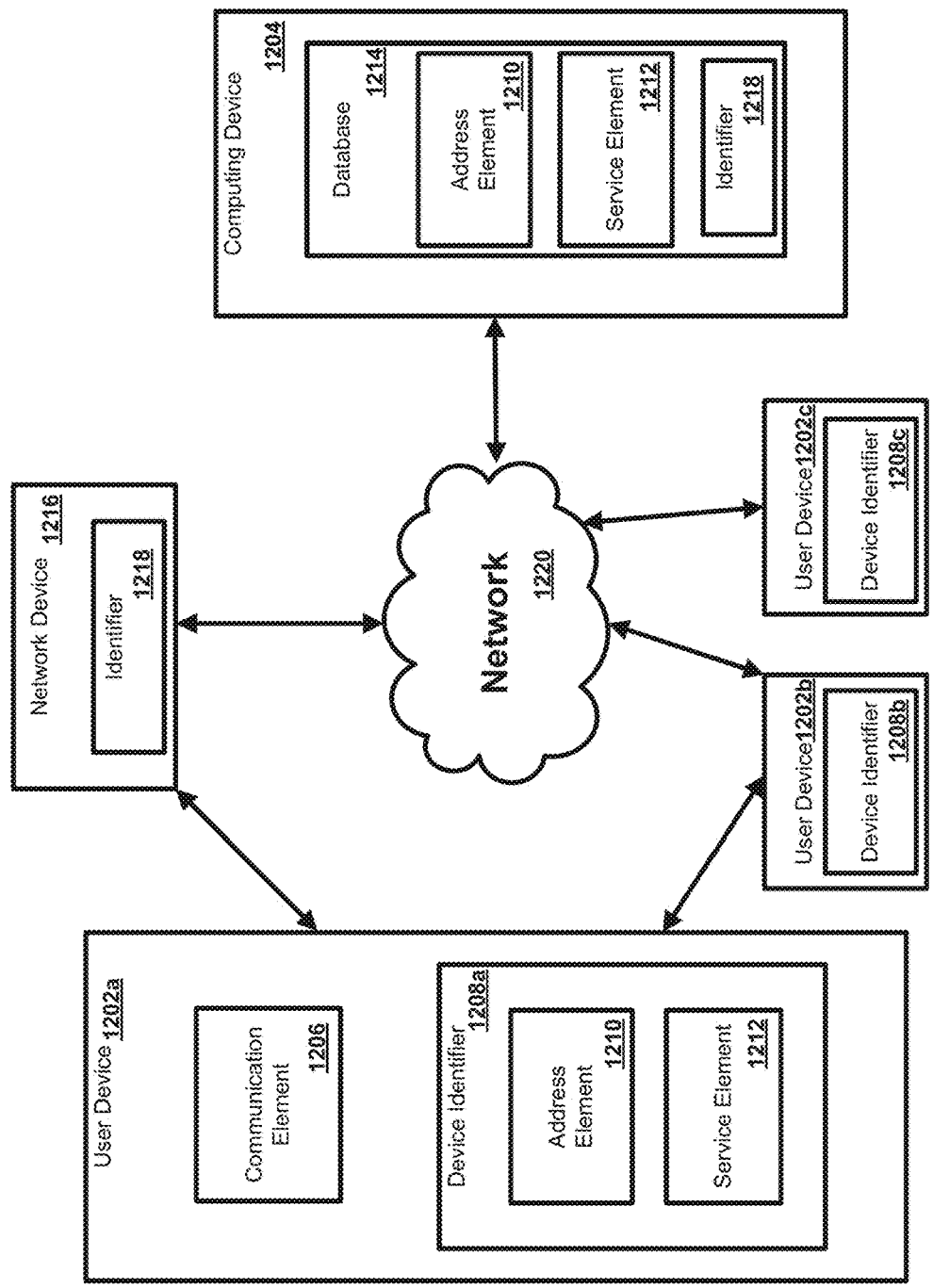
FIG. 12 is a diagram of one embodiment of a networked system used in connection with an electronic vaporizing device according to some embodiments.

In one embodiment of the disclosure, a system may be configured to provide services such as network-related services to a user device. FIG. 12 illustrates various embodiments of an exemplary environment in which the present methods and systems may operate. The present disclosure is relevant to systems and methods for providing services to a user device, for example, electronic vapor devices which may include, but are not limited to, a vape-bot, micro-vapor device, vapor pipe, e-cigarette, hybrid handset and vapor device, and the like. Other user devices that may be used in the systems and methods include, but are not limited to, a smart watch (and any other form of "smart" wearable technology), a smartphone, a tablet, a laptop, a desktop, a personal computing device, and the like. In an embodiment, one or more network devices may be configured to provide various services to one or more devices, such as devices located at or near a premises. In another embodiment, the network devices may be configured to recognize an authoritative device for the premises and/or a particular service or services available at the premises. As an example, an authoritative device may be configured to govern or enable connectivity to a network such as the Internet or other remote resources, provide address and/or configuration services like DHCP, and/or provide naming or service discovery services for a premises, or a combination thereof. Those skilled in the art will appreciate that present methods may be used in various types of networks and systems that employ both digital and analog equipment. One skilled in the art will appreciate that provided herein is a functional description and that the respective functions may be performed by software, hardware, or a combination of software and hardware.

The network and system may comprise a user device 1202a, 1202b, and/or 1202c in communication with a computing device 1204 such as a server, for example. The computing device 1204 may be disposed locally or remotely relative to the user device 1202a, 1202b, and/or 1202c. As an example, the user device 1202a, 1202b, and/or 1202c and the computing device 1204 may be in communication via a private and/or public network 1220 such as the Internet or a local area network. Other forms of communications may be used such as wired and wireless telecommunication channels, for example. In another embodiment, the user device 1202a, 1202b, and/or 1202c may communicate directly without the use of the network 1220 (for example, via Bluetooth®, infrared, and the like).

In an embodiment, the user device 1202a, 1202b, and/or 1202c may be an electronic device such as an electronic vapor device (e.g., vape-bot, micro-vapor device, vapor pipe, e-cigarette, hybrid handset and vapor device), a smartphone, a smart watch, a computer, a smartphone, a laptop, a tablet, a set top box, a display device, or other device capable of communicating with the computing device 1204. As an example, the user device 1202a, 1202b, and/or 1202c may comprise a communication element 1206 for providing an interface to a user to interact with the user device 1202a, 1202b, and/or 1202c and/or the computing device 1204. The communication element 1206 may be any interface for presenting and/or receiving information to/from the user, such as user feedback. An example interface may be communication interface such as a web browser (e.g., Internet Explorer, Mozilla Firefox, Google Chrome, Safari, or the like). Other software, hardware, and/or interfaces may be used to provide communication between the user and one or more of the user device 1202a, 1202b, and/or 1202c and the computing device 1204. In an embodiment, the user device 1202a, 1202b, and/or 1202c may have at least one similar interface quality such as a symbol, a voice activation protocol, a graphical coherence, a startup sequence continuity element of sound, light, vibration or symbol. In an embodiment, the interface may comprise at least one of lighted signal lights, gauges, boxes, forms, words, video, audio scrolling, user selection systems, vibrations, check marks, avatars, matrix', visual images, graphic designs, lists, active calibrations or calculations, 2D interactive fractal designs, 3D fractal designs, 2D and/or 3D representations of vapor devices and other interface system functions.

As an example, the communication element 1206 may request or query various files from a local source and/or a remote source. As a further example, the communication element 1206 may transmit data to a local or remote device such as the computing device 1204.

In an embodiment, the user device 1202a, 1202b, and/or 1202c may be associated with a user identifier or device identifier 1208a, 1208b, and/or 1208c. As an example, the device identifier 1208a, 1208b, and/or 1208c may be any identifier, token, character, string, or the like, for differentiating one user or user device (e.g., user device 1202a, 1202b, and/or 1202c) from another user or user device. In a further embodiment, the device identifier 1208a, 1208b, and/or 1208c may identify a user or user device as belonging to a particular class of users or user devices. As a further example, the device identifier 1208a, 1208b, and/or 1208c may comprise information relating to the user device such as a manufacturer, a model or type of device, a service provider associated with the user device 1202a, 1202b, and/or 1202c, a state of the user device 1202a, 1202b, and/or 1202c, a locator, and/or a label or classifier. Other information may be represented by the device identifier 1208a, 1208b, and/or 1208c.

In an embodiment, the device identifier 1208a, 1208b, and/or 1208c may comprise an address element 1210 and a service element 1212. In an embodiment, the address element 1210 may comprise or provide an internet protocol address, a network address, a media access control (MAC) address, an Internet address, or the like. As an example, the address element 1210 may be relied upon to establish a communication session between the user device 1202a, 1202b, and/or 1202c and the computing device 1204 or other devices and/or networks. As a further example, the address element 1210 may be used as an identifier or locator of the user device 1202a, 1202b, and/or 1202c. In an embodiment, the address element 1210 may be persistent for a particular network.

In an embodiment, the service element 1212 may comprise an identification of a service provider associated with the user device 1202a, 1202b, and/or 1202c and/or with the class of user device 1202a, 1202b, and/or 1202c. The class of the user device 1202a, 1202b, and/or 1202c may be related to a type of device, capability of device, type of service being provided, and/or a level of service. As an example, the service element 1212 may comprise information relating to or provided by a communication service provider (e.g., Internet service provider) that is providing or enabling data flow such as communication services to and/or between the user device 1202a, 1202b, and/or 1202c. As a further example, the service element 1212 may comprise information relating to a preferred service provider for one or more particular services relating to the user device 1202a, 1202b, and/or 1202c. In an embodiment, the address element 1210 may be used to identify or retrieve data from the service element 1212, or vice versa. As a further example, one or more of the address element 1210 and the service element 1212 may be stored remotely from the user device 1202a, 1202b, and/or 1202c and retrieved by one or more devices such as the user device 1202a, 1202b, and/or 1202c and the computing device 1204. Other information may be represented by the service element 1212.

In an embodiment, the computing device 1204 may be a server for communicating with the user device 1202a, 1202b, and/or 1202c. As an example, the computing device 1204 may communicate with the user device 1202a, 1202b, and/or 1202c for providing data and/or services. As an example, the computing device 1204 may provide services such as data sharing, data syncing, network (e.g., Internet) connectivity, network printing, media management (e.g., media server), content services, streaming services, broadband services, or other network-related services. In an embodiment, the computing device 1204 may allow the user device 1202a, 1202b, and/or 1202c to interact with remote resources such as data, devices, and files. As an example, the computing device may be configured as (or disposed at) a central location, which may receive content (e.g., data) from multiple sources, for example, user devices 1202a, 1202b, and/or 1202c. The computing device 1204 may combine the content from the multiple sources and may distribute the content to user (e.g., subscriber) locations via a distribution system In an embodiment, one or more network devices 1216 may be in communication with a network such as network 1220. As an example, one or more of the network devices 1216 may facilitate the connection of a device, such as user device 1202a, 1202b, and/or 1202c, to the network 1220. As a further example, one or more of the network devices 1216 may be configured as a wireless access point (WAP). In an embodiment, one or more network devices 1216 may be configured to allow one or more wireless devices to connect to a wired and/or wireless network using Wi-Fi, Bluetooth or any desired method or standard.

In an embodiment, the network devices 1216 may be configured as a local area network (LAN). As an example, one or more network devices 1216 may comprise a dual band wireless access point. As an example, the network devices 1216 may be configured with a first service set identifier (SSID) (e.g., associated with a user network or private network) to function as a local network for a particular user or users. As a further example, the network devices 1216 may be configured with a second service set identifier (SSID) (e.g., associated with a public/community network or a hidden network) to function as a secondary network or redundant network for connected communication devices.

In an embodiment, one or more network devices 1216 may comprise an identifier 1218. As an example, one or more identifiers may be or relate to an Internet Protocol (IP) Address IPV4/IPV6 or a media access control address (MAC address) or the like. As a further example, one or more identifiers 1218 may be a unique identifier for facilitating communications on the physical network segment. In an embodiment, each of the network devices 1216 may comprise a distinct identifier 1218. As an example, the identifiers 1218 may be associated with a physical location of the network devices 1216.

In an embodiment, the computing device 1204 may manage the communication between the user device 1202a, 1202b, and/or 1202c and a database 1214 for sending and receiving data there between. As an example, the database 1214 may store a plurality of files (e.g., web pages), user identifiers or records, or other information. In one embodiment, the database 1214 may store user device 1202a, 1202b, and/or 1202c usage information (including chronological usage), type of vaporizable and/or non-vaporizable material used, frequency of usage, location of usage, recommendations, communications (e.g., text messages, advertisements, photo messages), simultaneous use of multiple devices, and the like). The database 1214 may collect and store data to support cohesive use, wherein cohesive use is indicative of the use of a first electronic vapor devices and then a second electronic vapor device is synced chronologically and logically to provide the proper specific properties and amount of vapor based upon a designed usage cycle. As a further example, the user device 1202a, 1202b, and/or 1202c may request and/or retrieve a file from the database 1214. The user device 1202a, 1202b, and/or 1202c may thus sync locally stored data with more current data available from the database 1214. Such syncing may be set to occur automatically on a set time schedule, on demand, and/or in real-time. The computing device 1204 may be configured to control syncing functionality. For example, a user may select one or more of the user device 1202a, 1202b, and/or 1202c to never by synced, to be the master data source for syncing, and the like. Such functionality may be configured to be controlled by a master user and any other user authorized by the master user or agreement. The database 1214 may be further configured to store vehicle status data. The database 1214 may store the vehicle status data and identify which user device 1202a, 1202b, and/or 1202c generated the vehicle status data. Thus, the database 1214 may comprise a compilation of vehicle status data from multiple devices. The vehicle status data may be distributed amongst the user device 1202a, 1202b, and/or 1202c along with any other electronic device. The vehicle status data may be used to report vehicle performance and/or used to predict future vehicle performance.

In an embodiment, data may be derived by system and/or device analysis. Such analysis may comprise at least by one of instant analysis performed by the user device 1202a, 1202b, and/or 1202c or archival data transmitted to a third party for analysis and returned to the user device 1202a, 1202b, and/or 1202c and/or computing device 1204. The result of either data analysis may be communicated to a user of the user device 1202a, 1202b, and/or 1202c to, for example, inform the user of their electronic vaporizing use and/or lifestyle options. In an embodiment, a result may be transmitted back to at least one authorized user interface.

In an embodiment, the database 1214 may store information relating to the user device 1202a, 1202b, and/or 1202c such as the address element 1210 and/or the service element 1212. As an example, the computing device 1204 may obtain the device identifier 1208a, 1208b, and/or 1208c from the user device 1202a, 1202b, and/or 1202c and retrieve information from the database 1214 such as the address element 1210 and/or the service elements 1212. As a further example, the computing device 1204 may obtain the address element 1210 from the user device 1202a, 1202b, and/or 1202c and may retrieve the service element 1212 from the database 1214, or vice versa. Any information may be stored in and retrieved from the database 1214. The database 1214 may be disposed remotely from the computing device 1204 and accessed via direct or indirect connection. The database 1214 may be integrated with the computing device 1204 or some other device or system.

Figure 13:
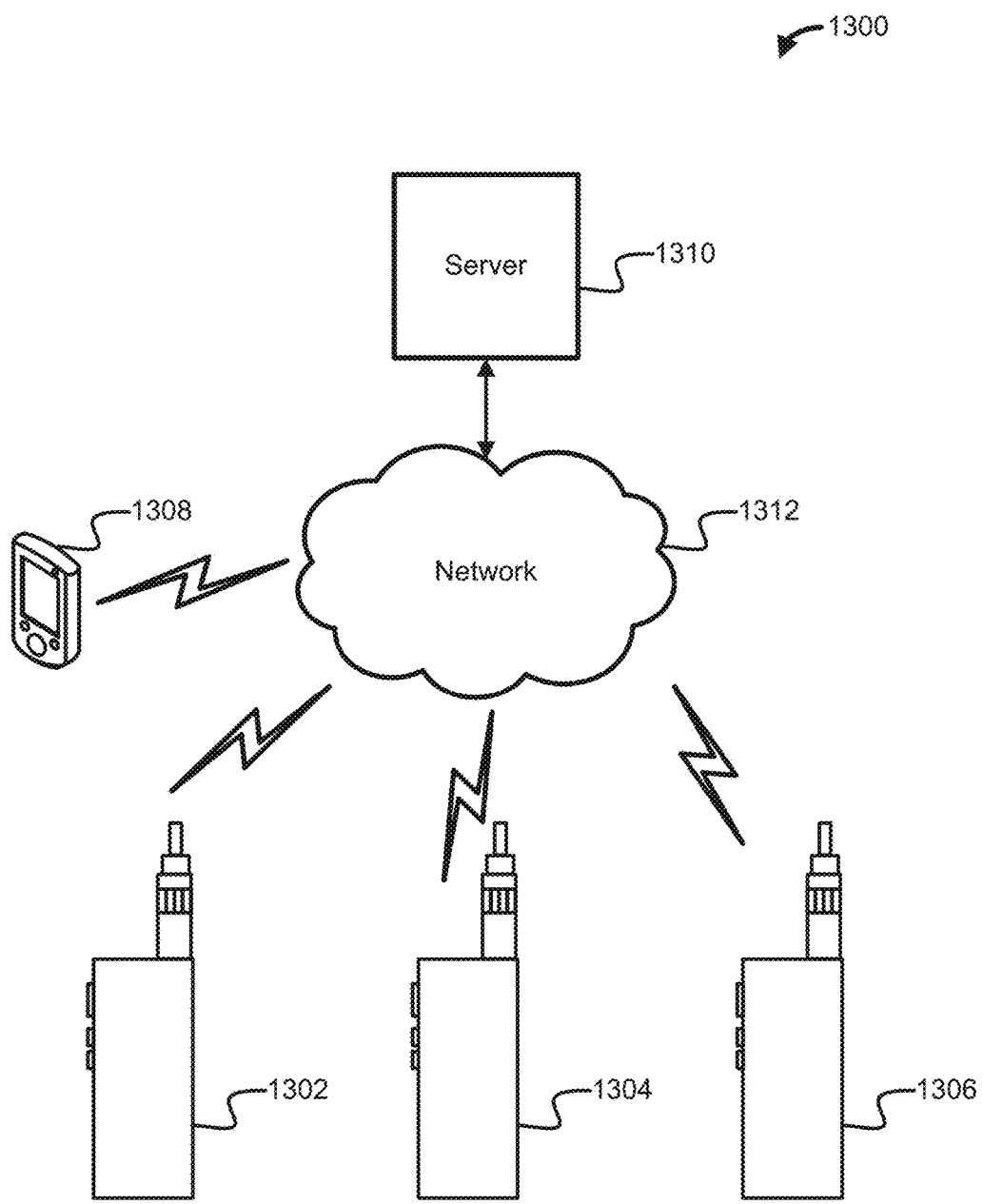
FIG. 13 is a diagram of one embodiment of a networked system used in connection with an electronic vaporizing device according to some embodiments.

FIG. 13 illustrates an ecosystem 1300 configured for sharing and/or syncing data such as vehicle-related information, usage information (including chronological usage), type of vaporizable and/or non-vaporizable material used, frequency of usage, location of usage, recommendations, communications (e.g., text messages, advertisements, photo messages), simultaneous use of multiple devices, and the like) between one or more devices such as a vapor device 1302, a vapor device 1304, a vapor device 1306, and an electronic communication device 1308. In an embodiment, the vapor device 1302, the vapor device 1304, the vapor device 1306 may be one or more of an electronic cigarette, an electronic cigar, an electronic vapor modified device, a hybrid electronic communication handset coupled/integrated vapor device, a micro-sized electronic vapor device, or a robotic vapor device. In an embodiment, the electronic communication device 1308 may comprise one or more of a smartphone, a smart watch, a tablet, a laptop, personal computing device, and the like.

In an embodiment data generated, gathered, created, etc., by one or more of the vapor device 1302, the vapor device 1304, the vapor device 1306, and/or the electronic communication device 1308 may be uploaded to and/or downloaded from a central server 1310 via a network 1312, such as the Internet. Such uploading and/or downloading may be performed via any form of communication including wired and/or wireless. In an embodiment, the vapor device 1302, the vapor device 1304, the vapor device 1306, and/or the electronic communication device 1308 may be configured to communicate via cellular communication, Wi-Fi communication, Bluetooth® communication, satellite communication, and the like.

The central server 1310 may store uploaded data and associate the uploaded data with a user and/or device that uploaded the data. The central server 1310 may access unified account and tracking information to determine devices that are associated with each other, for example devices that are owned/used by the same user. The central server 1310 may utilize the unified account and tracking information to determine which of the vapor device 1302, the vapor device 1304, the vapor device 1306, and/or the electronic communication device 1308, if any, should receive data uploaded to the central server 1310.

For example, the vapor device 1302 may be configured to upload usage information related to vaporizable material consumed and the electronic communication device 1308 may be configured to upload location information related to location of the vapor device 1302. The central server 1310 may receive both the usage information and the location information, access the unified account and tracking information to determine that both the vapor device 1302 and the electronic communication device 1308 are associated with the same user. The central server 1310 may thus correlate the user's location along with the type, amount, and/or timing of usage of the vaporizable material. The central server 1310 may further determine which of the other devices are permitted to receive such information and transmit the information based on the determined permissions. In an embodiment, the central server 1310 may transmit the correlated information to the electronic communication device 1308 which may then subsequently use the correlated information to recommend a specific type of vaporizable material to the user when the user is located in the same geographic position indicated by the location information. In an embodiment, the vapor device 1302 may be configured to upload vehicle-related information. The central server 1310 may correlate the vehicle-related information with the usage information and/or the location information. The correlated information may be transmitted to any device in the ecosystem 1300.

In another embodiment, the central server 1310 may provide one or more social networking services for users of the vapor device 1302, the vapor device 1304, the vapor device 1306, and/or the electronic communication device 1308. Such social networking services include, but are not limited to, messaging (e.g., text, image, and/or video), mixture sharing, product recommendations, location sharing, product ordering, and the like.

In one embodiment, illustrated in FIG. 14A, FIG. 14B, and FIG. 14C, there may be provided an example vapor device 1400. As shown in FIG. 14A, the vapor device 1400 may comprise an electronic communication device 1402 and a detachable vaporizer 1404. In one embodiment, the electronic communication device may be a device that is only capable of communicating with other devices via text (e.g., no telephone capabilities). The text-only electronic communication device 1402 may comprise a keyboard 1428 (or other input, such as an onscreen keyboard) and a screen 1430. A user may use the keyboard 1428 to send a message to other users. In one embodiment, the electronic communication device 1402 may comprise a messaging application (e.g., an instant messaging application) and/or a Short Message Service application. The electronic communication device 1402 may comprise one or more components of the electronic vaporizing device 100 (described in FIG. 1, a processor 102, a network access device 106, a memory 104, and the like) necessary to provide communication functionality.

In one embodiment, the electronic communication device 1402 may be used as a standalone communication device. In another embodiment, the electronic communication device 1402 and the detachable vaporizer 1404 may connect via an input/output port 1406 on the electronic communication device 1402 and an input/output port 1408 on the detachable vaporizer 1404. The electronic communication device input/output port 1406 and the vaporizer input/output port 1408 may adhere to any proprietary standard. The electronic communication device input/output port 1406 and the vaporizer input/output port 1408 may comprise one or more of a USB connection, a dock connector (e.g., 20-24-30 pin connectors, lightening port connection, etc.), Portable Digital Media Interface, and the like. The electronic communication device input/output port 1406 and the vaporizer input/output port 1408 may be used to pass power and/or data between the electronic communication device 1402 and the detachable vaporizer 1404.

The detachable vaporizer 1404 may comprise a vaporize button 1410 that may be configured to initiate a process of vaporizing a vaporizable material contained within the detachable vaporizer 1404, resulting in vapor exiting an exhaust port 1412 for inhalation by a user. The exhaust port 1412 may be hingedly attached to the detachable vaporizer 1404 to enable the exhaust port 1412 to be stored within a housing of the detachable vaporizer 1404. The detachable vaporizer 1404 may comprise an exhaust port release button 1414 to disengage the exhaust port 1412 when stored and locked within the housing of the detachable vaporizer 1404. FIG. 14B illustrates the vapor device 1400 after the electronic communication device 1402 and the detachable vaporizer 1404 have been coupled via the electronic communication device input/output port 1406 and the vaporizer input/output port 1408. The detachable vaporizer 1404 may comprise a locking mechanism 1416. The locking mechanism 1416 may be configured to secure the detachable vaporizer 1404 to the electronic communication device 1402.

FIG. 14C illustrates the detachable vaporizer 1404. In one embodiment, the detachable vaporizer 1404 may comprise the vaporizer disclosed herein and as illustrated in FIG. 1. The detachable vaporizer 1404 may receive air through an input/output component 1418. The received air may pass into a mixing chamber 1420. The detachable vaporizer 1404 may comprise or be coupled to one or more containers 1410 containing a vaporizable material, such as a fluid. A wick 1424, or a valve, may couple the one or more containers 1410 to the mixing chamber 1420. The coupling may operate independently of gravity, such as by capillary action or pressure drop through a valve. The detachable vaporizer 1404 may be configured to vaporize the vaporizable material from the one or more containers 1410 at controlled rates in response to mechanical input from the vaporize button 1422 and/or in response to signals received from the electronic communication device 1402 or another component. Vaporizable material (e.g., fluid) may be supplied by one or more replaceable cartridges. If the vaporizable material is liquid, the cartridge may comprise the wick 1424 to aid in transporting the liquid to the mixing chamber 1420. In the alternative, some other transport mode may be used. In one embodiment, one or more materials may be vaporized at a single time by the detachable vaporizer 1404.

In operation, a heating element 1426 may vaporize or nebulize the vaporizable material in the mixing chamber 1420, producing an inhalable vapor/mist that may be expelled via the exhaust port 1412. In one embodiment, the heating element 1426 may comprise a nickel-chromium wire or the like, with a temperature sensor (not shown), such as a thermistor or thermocouple. Within definable limits, by controlling the power to the wick 1424, a rate of vaporization may be independently controlled. The heating element 1426 may receive power through the electronic communication device input/output port 1406 and the vaporizer input/output port 1408. For example, the heating element 1426 may receive power from a power supply built into the electronic communication device 1402. The heating element 1426 may vaporize or nebulizer the vaporizable material in the mixing chamber 1420. The detachable vaporizer 1404 may exchange data signals with a processor of the electronic communication device 1402 through the electronic communication device input/output port 1406 and the vaporizer input/output port 1408 for control of the detachable vaporizer 1404.

Figure 15:
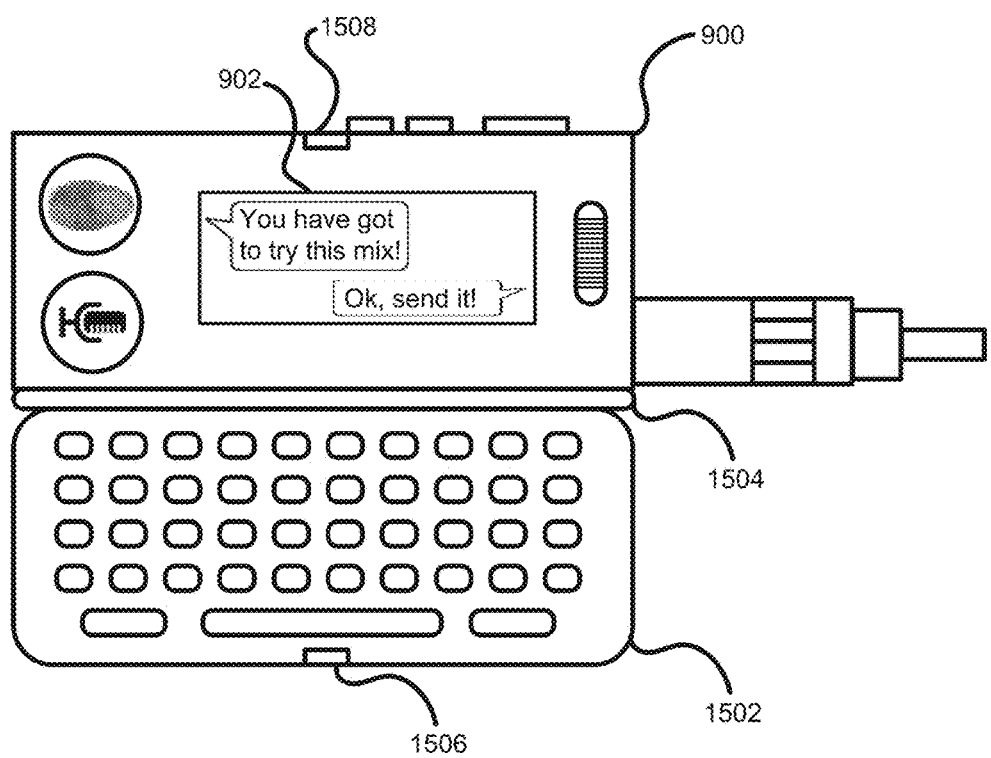
FIG. 15 is a diagram of one embodiment of an electronic vaporizing device according to some embodiments.

FIG. 15 illustrates the example vapor device 900 with an attached keyboard 1502. The vapor device 900 may be configured for text-only messaging as shown on the display 902. The keyboard 1502 may be attached to the vapor device 900 via a hinge 1504. The hinge 1504 enables the keyboard 1502 to be secured to the vapor device 900 via a tab 1506 that may be securely received by a slot 1508. When closed, the keyboard 1502 may thus protect the display 902. Although hinge 1504 is preferably a hinge, it can be a non-hinge connector.

Figure 16:
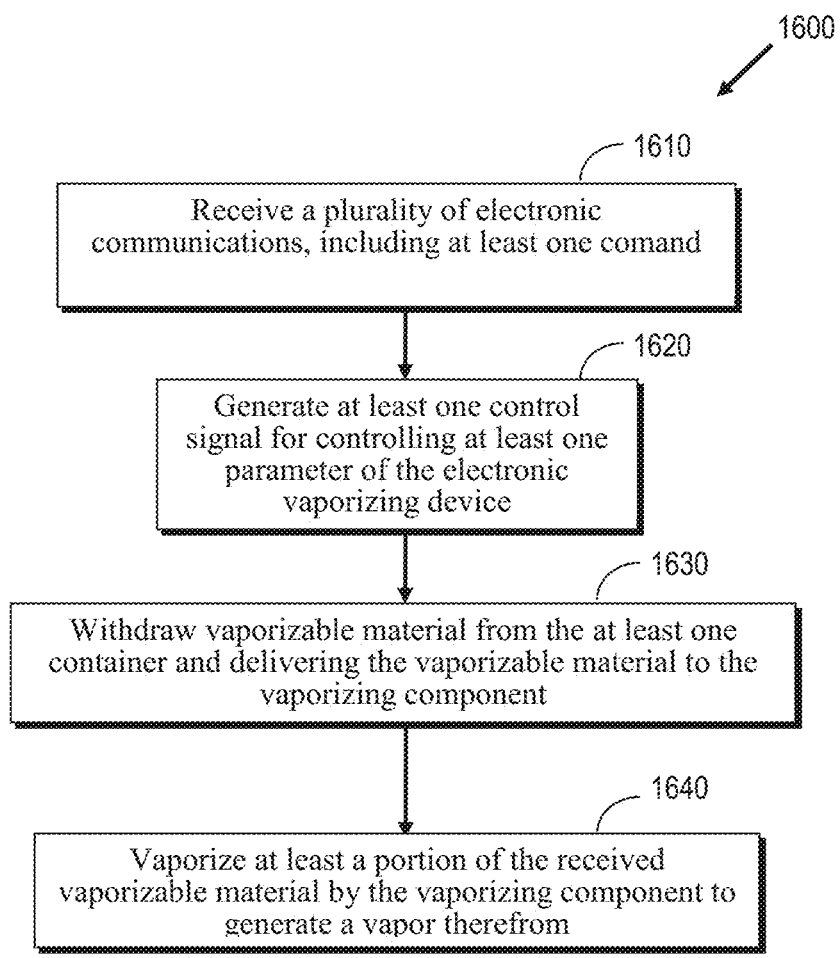
FIG. 16 is a flow block diagram of one embodiment of a method operating an electronic vaporizing device having messaging functionality according to some embodiments.

In an embodiment, illustrated in FIG. 16, a method 1600 may be provided for vaporizing at least one vaporizable material by an electronic vaporizing device, wherein the electronic vaporizing device may comprise (a) a plurality of containers, wherein at least one of the plurality of containers contains a vaporizable material; (b) a mixing component operable to control a selected amount of vaporizable material to be withdrawn from the at least one container; (c) a vaporizing component comprising an ultrasonic vibration element operable to produce ultrasonic vibrations to vaporize a plurality of materials received therein, and a heating element operable to produce heat energy to vaporize a plurality of materials received therein; and (d) at least one power source operatively coupled to the mixing component and the vaporizing component.

The method may comprise the step 1610 of receiving, from the electronic communication device 150, a plurality of electronic communications. The plurality of received communications may comprise at least one of an instant message, a Short Message Service message, a Multimedia Messaging Service message, and an Enhanced Messaging Service message. At least one of the received communications may include at least one command for controlling at least one operational parameter of the electronic vaporizing device 100.

The method may further comprise the step 1620 of generating, by the processor 102, at least one control signal for controlling at least one operational parameter of the electronic vaporizing device 100 based on the at least one received command. In one embodiment, the processor 102 may generate at least one mixing control signal for controlling an amount of vaporizable material to be withdrawn from a selected number of the plurality of containers 110 by the mixing component 122 based on the at least one command. The at least one command may include at least one of an identification of a selected number of the plurality of containers from which vaporizable material is to be withdrawn, the selected amount of vaporizable material to be withdrawn from the selected number of the plurality of containers, a timing of the withdrawal, a rate of the withdrawal, and combinations thereof.

The method may also comprise the step 1630 of withdrawing, by the mixing component 122, a selected amount of vaporizable material from the at least one container 110 in accordance with the at least one control signal and delivering the selected amount of vaporizable material withdrawn therefrom to the vaporizing component 108. The method may further comprise the step 1640 of vaporizing at least a portion of the received vaporizable material by the vaporizing component 108 in accordance with the at least one control signal to generate a vapor therefrom.

In another embodiment, the method may further comprise receiving a plurality of electronic communications from the at least one network, wherein the plurality of received communications may comprise at least one of an instant message, a Short Message Service message, a Multimedia Messaging Service message, and an Enhanced Messaging Service message receiving, by the electronic communication device, and wherein at least one of the received communications may include at least one command for controlling at least one operational parameter of the electronic vaporizing device.

The electronic vaporizing device may be suitably selected from the group of electronic vaporizing devices consisting of an electronic cigarette, an electronic cigar, an electronic vapor device, an electronic vapor device integrated with an electronic communication device, a robotic vapor device, and/or a micro-size electronic vapor device.

In view of the exemplary systems described herein, methodologies that may be implemented in accordance with the disclosed subject matter have been described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described herein. Additionally, it should be further appreciated that the methodologies disclosed herein are capable of being stored on an article of manufacture to facilitate transporting and transferring such methodologies to computers.

Those of ordinary skill in the relevant art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

As used in this application, the terms "component," "module," "system," and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server may be a component. One or more components may reside within a process and/or thread of execution and a component may be localized on one computer and/or distributed between two or more computers.

As used herein, a "vapor" includes mixtures of a carrier gas or gaseous mixture (for example, air) with any one or more of a dissolved gas, suspended solid particles, or suspended liquid droplets, wherein a substantial fraction of the particles or droplets if present are characterized by an average diameter of not greater than three microns. As used herein, an "aerosol" has the same meaning as "vapor," except for requiring the presence of at least one of particles or droplets. A substantial fraction means 10% or greater; however, it should be appreciated that higher fractions of small (<3 micron) particles or droplets may be desirable, up to and including 100%. It should further be appreciated that, to simulate smoke, average particle or droplet size may be less than three microns, for example, may be less than one micron with particles or droplets distributed in the range of 0.01 to 1 micron. A vaporizer may include any device or assembly that produces a vapor or aerosol from a carrier gas or gaseous mixture and at least one vaporizable material. An aerosolizer is a species of vaporizer, and as such is included in the meaning of vaporizer as used herein, except where specifically disclaimed.

Various embodiments presented in terms of systems may comprise a number of components, modules, and the like. It is to be understood and appreciated that the various systems may include additional components, modules, etc. and/or may not include all of the components, modules, etc. discussed in connection with the figures. A combination of these approaches may also be used.

In addition, the various illustrative logical blocks, modules, and circuits described in connection with certain embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, system-on-a-chip, or state machine. A processor may also be implemented as a combination of computing devices, e.g., a combination of a DSP and a microprocessor, a plurality of microprocessors, one or more microprocessors in conjunction with a DSP core, or any other such configuration.

Operational embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, a DVD disk, or any other form of storage medium known in the art. An exemplary storage medium is coupled to the processor such the processor may read information from, and write information to, the storage medium. In the alternative, the storage medium may be integral to the processor. The processor and the storage medium may reside in an ASIC or may reside as discrete components in another device.

Furthermore, the one or more versions may be implemented as a method, apparatus, or article of manufacture using standard programming and/or engineering techniques to produce software, firmware, hardware, or any combination thereof to control a computer to implement the disclosed embodiments. Non-transitory computer readable media may include but are not limited to magnetic storage devices (e.g., hard disk, floppy disk, magnetic strips), optical disks (e.g., compact disk (CD), digital versatile disk (DVD)), smart cards, and flash memory devices (e.g., card, stick). Those skilled in the art will recognize many modifications may be made to this configuration without departing from the scope of the disclosed embodiments.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those of ordinary skill in the art that various modifications and variations may be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A personal vaporizer comprising:
   a device processor operable for controlling the personal vaporizer;
   at least one container for storing a vaporizable liquid composition;
   a vaporizing component operatively coupled to the device processor and controlled in part by the device processor, wherein the vaporizing component is in fluid communication with the at least one container for receiving at least a portion of the vaporizable liquid composition therefrom, wherein the vaporizing component is operable to vaporize the vaporizable liquid composition received therein;
   a vapor outlet coupled to the vaporizing component and configured to receive a vapor generated by the vaporizing component, the vapor outlet operable to expel the generated vapor from the vaporizing device;
   an input/output device operatively coupled to the device processor and configured to operatively connect the device processor to an associated electronic communication device, wherein the input/output device is configured to receive a plurality of electronic communications from the associated electronic communication device, wherein at least one of the plurality of received communications comprises at least one command for controlling at least one operational parameter of the personal vaporizer, wherein the input/output device is configured to transmit the at least one command to the device processor for controlling the at least one operational parameter of the personal vaporizer; and
   a power source operatively coupled to the vaporizing component, wherein the at least one power source is operable to generate a supply of power for at least operation of the vaporizing component.

2. The personal vaporizer of claim 1, wherein the device processor is operable to generate at least one control signal for controlling the at least one operational parameter of the personal vaporizer based on the at least one command.

3. The personal vaporizer of claim 2, wherein the device processor is operable to generate at least one vaporizing control signal for selectively operating the vaporizing component.

4. The personal vaporizer of claim 3, wherein the at least one vaporizing control signal for selectively operating the vaporizing component is based on a type of vaporizable liquid composition stored in the at least one container.

5. The personal vaporizer of claim 1, wherein the at least one command comprises at least one device activation parameter for controlling activation of the vaporization process;
   wherein the device processor is further operable to:
   receive that at least one device activation parameters for controlling activation of the vaporization process;

generate at least one device activation control signal in accordance with the at least one device activation parameter; and transmit the at least one device activation control signal to the vaporizing component to initiate the vaporization process in accordance the at least one device activation control signal.

6. The personal vaporizer of claim 1, wherein the vaporizing component comprises an ultrasonic vibration element operable to produce ultrasonic vibrations to vaporize at least a portion of the vaporizable liquid composition received therein.

7. The personal vaporizer of claim 6, wherein the ultrasonic vibration element comprises at least one piezoelectric dispersing element.

8. The personal vaporizer of claim 7, wherein the at least one piezoelectric dispersing element comprises at least one piezoelectric material selected from the group of piezoelectric material consisting of natural piezoelectric crystals, synthetic piezoelectric crystals, synthetic piezoelectric ceramics, and combinations thereof.

9. The personal vaporizer of claim 1, wherein the at least one container stores a water-based liquid composition that is substantially free of at least one of propylene glycol and vegetable glycerin.

10. A method for vaporizing a vaporizable liquid composition by a personal vaporizer, wherein the personal vaporizer comprises (a) a device processor operable to control the personal vaporizer;

(b) at least one container containing a vaporizable liquid composition;

(c) a vaporizing component operable to vaporize at least a portion of the vaporizable liquid composition received therein;

(e) an input/output device configured to receive a plurality of data for transmission to the device processor and to transmit a plurality of data generated by the device processor; and (f) a power source operable to generate an electrical current for operation of the vaporizing component, the method comprising:

receiving, from an associated electronic communication device, a plurality of electronic communications, wherein at least one of the received electronic communications comprises at least one command for controlling at least one operational parameter of the personal vaporizer;

generating, by the device processor, at least one control signal for controlling the at least one operational parameter of the personal vaporizer based on the at least one command;

withdrawing a selected amount of vaporizable liquid composition from the at least one container in accordance with the at least one control signal and delivering the selected amount of vaporizable liquid composition to the vaporizing component; and vaporizing at least a portion of the selected amount of vaporizable liquid composition by the vaporizing component in accordance with the at least one control signal.

11. The method of claim 10, generating, by the device processor, at least one control signal for controlling the at least one operational parameter of the personal vaporizer based on the at least one command.

12. The method of claim 11, generating, by the device processor, at least one vaporizing control signal for selectively operating the vaporizing component.

13. The method of claim 12, wherein the at least one vaporizing control signal for selectively operating the vaporizing component is based on a type of vaporizable liquid composition stored in the at least one container.

14. The method of claim 10, wherein the at least one command comprises at least one device activation parameter for controlling activation of the vaporization process, the method further comprising:

receiving, by the device processor, that at least one device activation parameters for controlling activation of the vaporization process;

generating, by the device processor, at least one device activation control signal in accordance with the at least one device activation parameter; and transmitting, by the device processor, the at least one device activation control signal to the vaporizing component to initiate the vaporization process in accordance the at least one device activation control signal.

15. The method of claim 10, wherein the vaporizing component comprises an ultrasonic vibration element operable to produce ultrasonic vibrations to vaporize at least a portion of the vaporizable liquid composition received therein.

16. The method of claim 15, wherein the ultrasonic vibration element comprises at least one piezoelectric dispersing element.

17. The method of claim 16, wherein the at least one piezoelectric dispersing element comprises at least one piezoelectric material selected from the group of piezoelectric material consisting of natural piezoelectric crystals, synthetic piezoelectric crystals, synthetic piezoelectric ceramics, and combinations thereof.

18. The method of claim 10, wherein the at least one container stores a water-based liquid composition that is substantially free of at least one of propylene glycol and vegetable glycerin.

* * * * *